US012048773B2

(12) United States Patent
Gross et al.

(10) Patent No.: US 12,048,773 B2
(45) Date of Patent: Jul. 30, 2024

(54) SELF-SANITIZING WAVEGUIDING SURFACES

(71) Applicant: HRL LABORATORIES, LLC, Malibu, CA (US)

(72) Inventors: Adam F. Gross, Santa Monica, CA (US); Kevin Geary, Santa Monica, CA (US); Shanying Cui, Calabasas, CA (US)

(73) Assignee: HRL LABORATORIES, LLC, Malibu, CA (US)

( * ) Notice: Subject to any disclaimer, the term of this patent is extended or adjusted under 35 U.S.C. 154(b) by 0 days.

(21) Appl. No.: 18/464,884

(22) Filed: Sep. 11, 2023

(65) Prior Publication Data
US 2023/0414809 A1 Dec. 28, 2023

Related U.S. Application Data

(62) Division of application No. 17/036,474, filed on Sep. 29, 2020, now Pat. No. 11,793,897, which is a (Continued)

(51) Int. Cl.
*A61L 2/10* (2006.01)
*A61L 2/238* (2006.01)
(Continued)

(52) U.S. Cl.
CPC ............... *A61L 2/10* (2013.01); *A61L 2/238* (2013.01); *A61L 2/26* (2013.01); *G02B 5/008* (2013.01);
(Continued)

(58) Field of Classification Search
CPC ... A61L 2/10; A61L 2/238; A61L 2/26; A61L 2202/11; G02B 6/102; G02B 5/008;
(Continued)

(56) References Cited

U.S. PATENT DOCUMENTS 10,279,059 B2    5/2019  Bettles et al.
2006/0002675 A1  1/2006  Choi et al.
(Continued)

OTHER PUBLICATIONS

Hodges, Sarah, et al., "UV Light Wand for Elimination of Bacteria Found in Pediatric Endotracheal Tubes," Presentation/Speech, Feb. 24, 2010, 24 pgs.; http://research.vuse.vanderbilt.edu/srdesign/2010/group10/Progress%20Reports/Oral_Presentation_3_Feb._24.pdf.
(Continued)

*Primary Examiner* — Sean E Conley
*Assistant Examiner* — Brendan A Hensel
(74) *Attorney, Agent, or Firm* — Lewis Roca Rothgerber Christie LLP

(57) ABSTRACT

A self-sanitizing surface structure configured to selectively refract light, a method of fabricating a self-sanitizing surface configured to selectively refract light, and a method of decontaminating a surface using selectively refracted light. A waveguide including a support layer below a propagating layer is positioned over a substrate as a self-sanitizing layer. In the absence of a contaminant or residue on the waveguide, UV light injected into the propagating layer is constrained within the propagating layer due to total internal reflection. When a residue is present on the self-sanitizing surface structure, light may be selectively refracted at or near the interface with the residue along the side of the waveguide to destroy the residue. The self-sanitizing surface structure may be configured is to refract a suitable amount of UV light in response to a particular type of residue or application.

6 Claims, 20 Drawing Sheets

Related U.S. Application Data division of application No. 15/870,082, filed on Jan. 12, 2018, now Pat. No. 10,821,198.

(60) Provisional application No. 62/461,415, filed on Feb. 21, 2017.

(51) Int. Cl.
*A61L 2/26* (2006.01)
*F21V 8/00* (2006.01)
*G02B 5/00* (2006.01)
*G02B 6/10* (2006.01)

(52) U.S. Cl.
CPC ......... *G02B 6/0023* (2013.01); *G02B 6/0065* (2013.01); *G02B 6/102* (2013.01); *A61L 2202/11* (2013.01); *G02B 6/003* (2013.01); *G02B 6/0043* (2013.01); *G02B 6/0066* (2013.01)

(58) Field of Classification Search
CPC .. G02B 6/0023; G02B 6/0065; G02B 6/0066; G02B 6/0043; G02B 6/003
See application file for complete search history.

(56) References Cited

U.S. PATENT DOCUMENTS

| | | | |
|---|---|---|---|
| 2007/0272877 A1* | 11/2007 | Tribelsky | A61L 9/205 250/431 |
| 2010/0209294 A1 | 8/2010 | Owen et al. | |
| 2011/0291995 A1* | 12/2011 | Shr | E05B 1/0069 250/492.1 |
| 2016/0074548 A1 | 3/2016 | Dobrinksy et al. | |
| 2017/0333580 A1 | 11/2017 | Cahan et al. | |
| 2018/0099061 A1 | 4/2018 | Asano | |

OTHER PUBLICATIONS

Maidecchi, Giulia, et al., "Deep Ultraviolet Plasmon Resonance in Aluminum Nanoparticle Arrays," ACSNANO, vol. 7, 2013, pp. 5834-5841.

Ye, Fan, et al., "Optical and electrical mappings of surface plasmon cavity modes," Nanophotonics 2014, 18 pgs., Science Wise Publishing & DeGruyter.

Doud, Devin F.R., et al., "In Situ UV Disinfection of a Waveguide-Based Photobioreactor," Environmental Science & Technology, 2014, vol. 48, pp. 11521-11526, ACS Publications.

Buonanno, Manuela, et al., "207-nm UV Light—A Promising Tool for Safe Low-Cost Reduction of Surgical Site Infections. I: In Vito Studies," PLOS ONE, Oct. 2013, vol. 8, Issue 10, e76968, pp. 1-7.

Shannon, Robert D., et al., "Refractive Index and Dispersion of Fluorides and Oxides," J. Phys. Chem. Ref. Data, vol. 31, No. 4. pp. 931-970, 2002.

Lorcheim, Kevin, "Ultraviolet Light for Disinfection," 7 pgs, 2015, https://www.laboratoryequipment.com/article/2015/08/ultraviolet-light-disinfection.

Zayats, Anatoly V., et al., "Nano-optics of surface plasmon polaritons," ScienceDirect, Physics Reports, vol. 408, Issues 3-4, pp. 131-314, 2005.

Peiris, Sunari, et al., "Metal nanoparticle photocatalysts: emerging processes for green organic synthesis," Catalysis Science & Technology, Issue 2, 2016, 47 pgs.

* cited by examiner

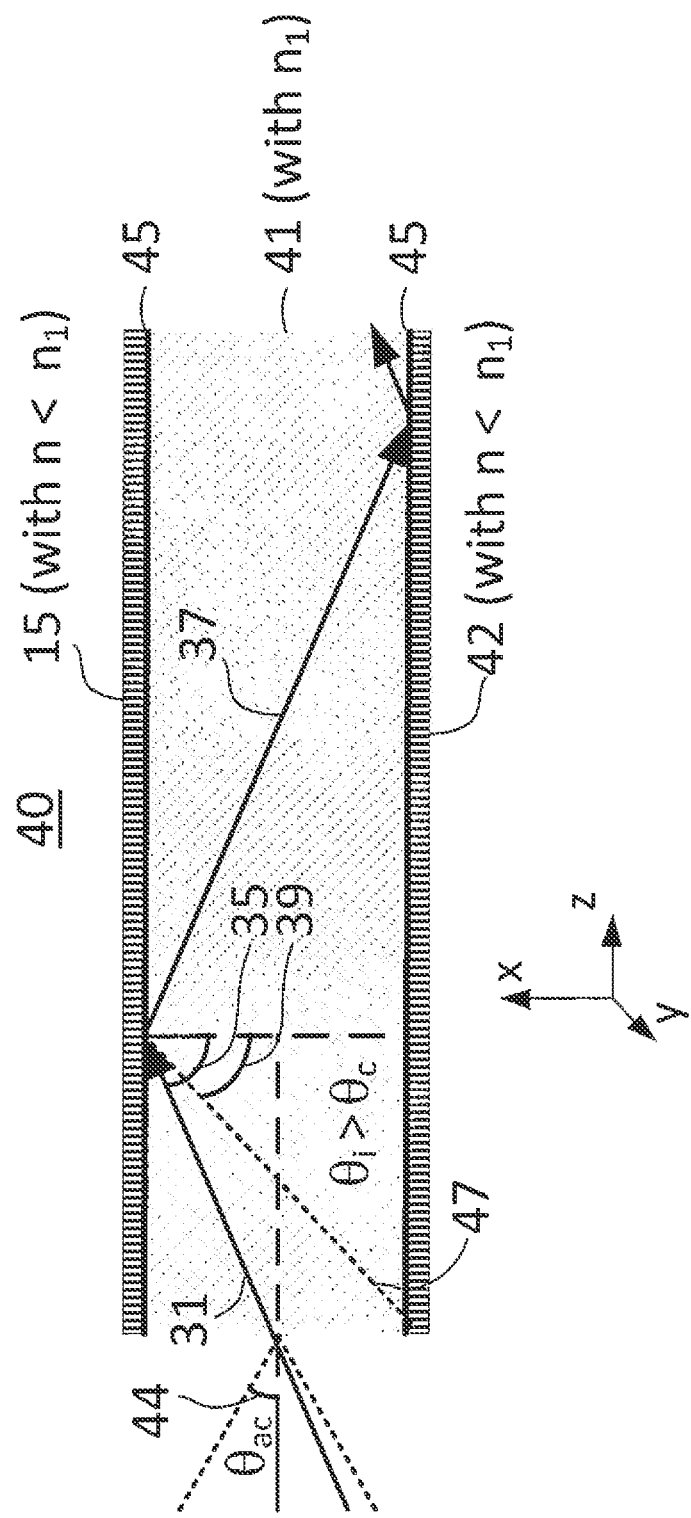

FIG. 8

Table 2.10 Dissociation energies of selected chemical bonds. The corresponding photon wavelengths are also shown [145]

| Chemical bond | Dissociation energy (eV) | Wavelength (nm) | Chemical bond | Dissociation energy (eV) | Wavelength (nm) |
|---|---|---|---|---|---|
| C=O | 7.5 | 165 | H–N | 4.1 | 302 |
| C=C | 6.4 | 194 | C–C | 3.6 | 344 |
| O=O | 5.1 | 243 | C–O | 3.6 | 344 |
| H–O | 4.8 | 258 | C–N | 3 | 413 |
| H–C | 4.3 | 288 | N–O | 2.2 | 564 |
| N=N | 4.3 | 288 | N–N | 1.6 | 775 |

FIG. 9

| Phosphorus | |
|---|---|
| P—P | 490(11) |
| P—Br | 266.5 |
| P—C | 513(8) |
| P—Cl | 289(42) |
| P—F | 439(96) |
| P—H | 343(29) |
| P—N | 617(21) |
| P—O | 596.6 |
| $Br_3P=O$ | 498(21) |
| $Cl_3P=O$ | 510(21) |
| $F_3P=O$ | 544(21) |
| P—S | 346.0(17) |
| P=S | 347 |
| P—Se | 363(10) |
| P—Te | 298(10) |

| Nitrogen | | Nitrogen (continued) | |
|---|---|---|---|
| N—N | 945.33(59) | N—I | 159(17) |
| N—Br | 276(21) | $F_2N-NF_2$ | 88(4) |
| ON—Br | 28.7(15) | $H_2N-NH_2$ | 297(8) |
| N—Cl | 389(50) | $H_2N-NHCH_3$ | 271 |
| ON—Cl | 159(6) | $H_2N-N(CH_3)_2$ | 264 |
| $O_2N$—Cl | 142(4) | $H_2N-NHC_6H_5$ | 213 |
| N—F | 301(42) | HN—$N_2$ | 38 |
| FN—F | 318(21) | ON—N | 480.7(42) |
| $F_2F$—N | 243(8) | ON—$NO_2$ | 39.8(8) |
| ON—F | 236(4) | $O_2N-NO_2$ | 57.3(21) |
| $O_2N$—F | 188(21) | HN=NH | 456(42) |
| | | N≡N | 946 |
| | | N—O | 630.57(13) |
| | | HN=O | 481 |
| | | NN—O | 167 |
| | | ON—O | 305 |
| | | N—P | 617(21) |
| | | N—S | 464(21) |

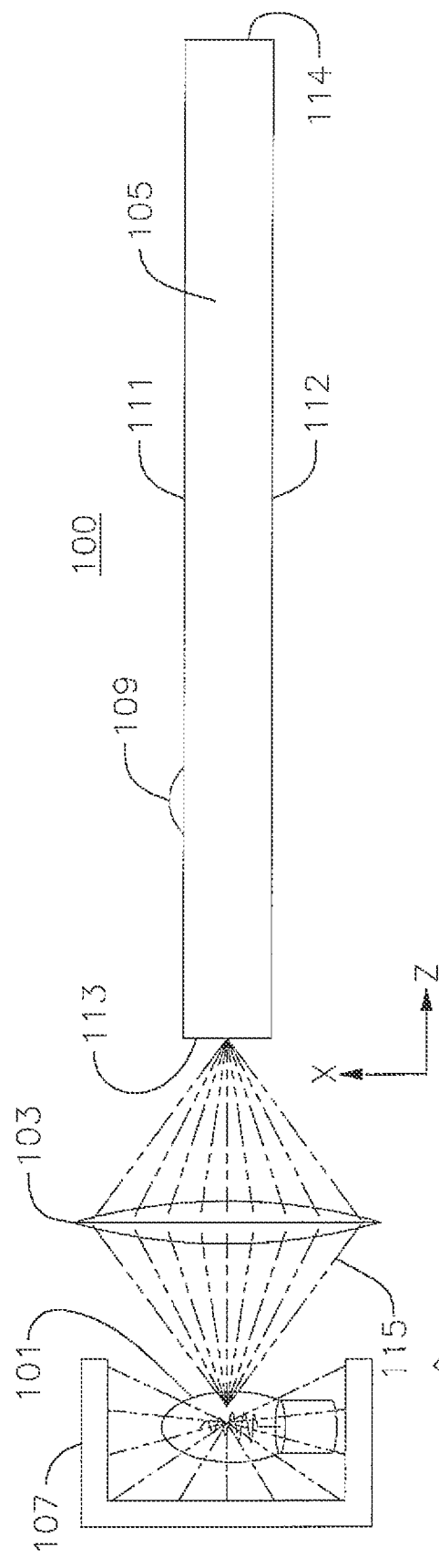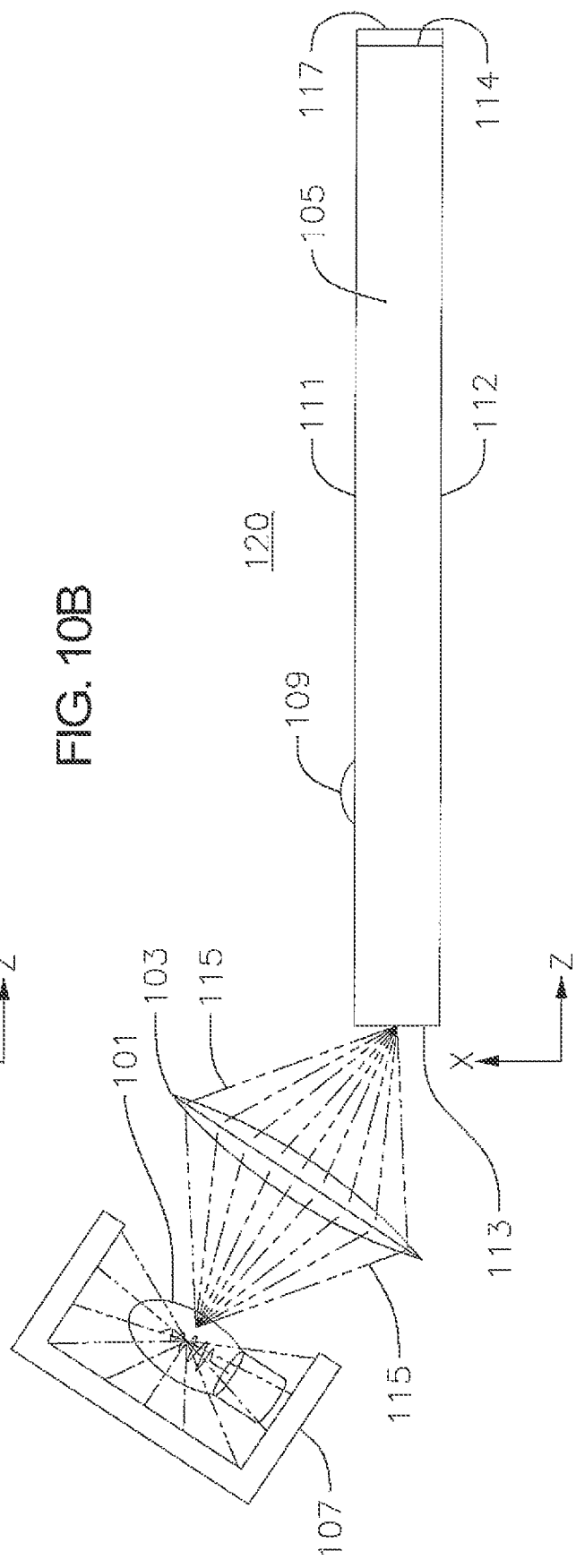

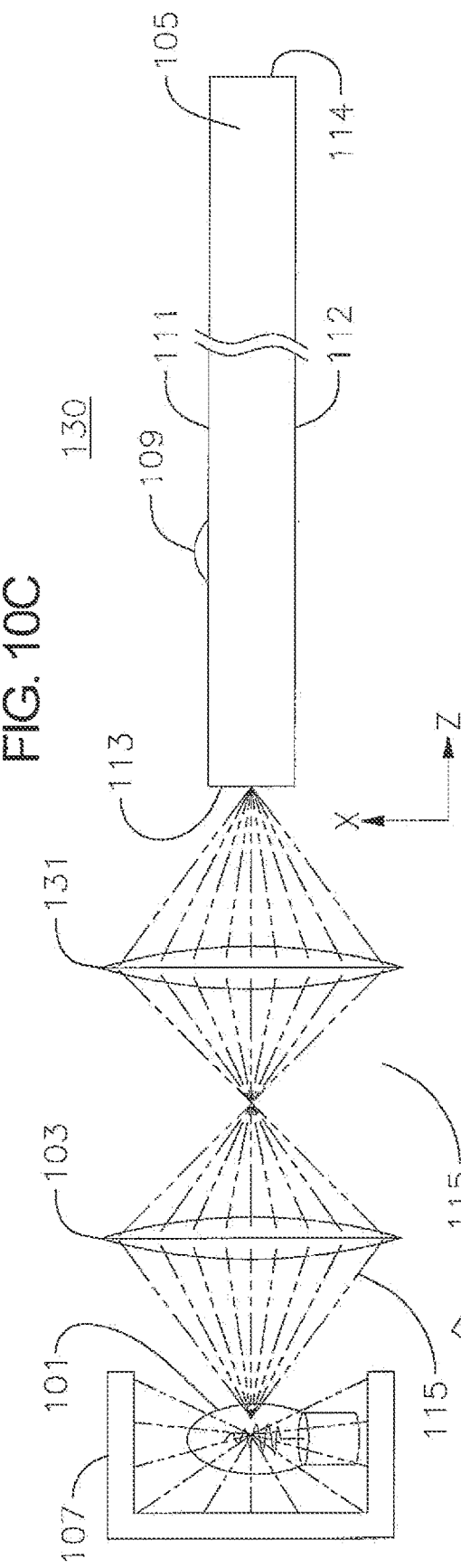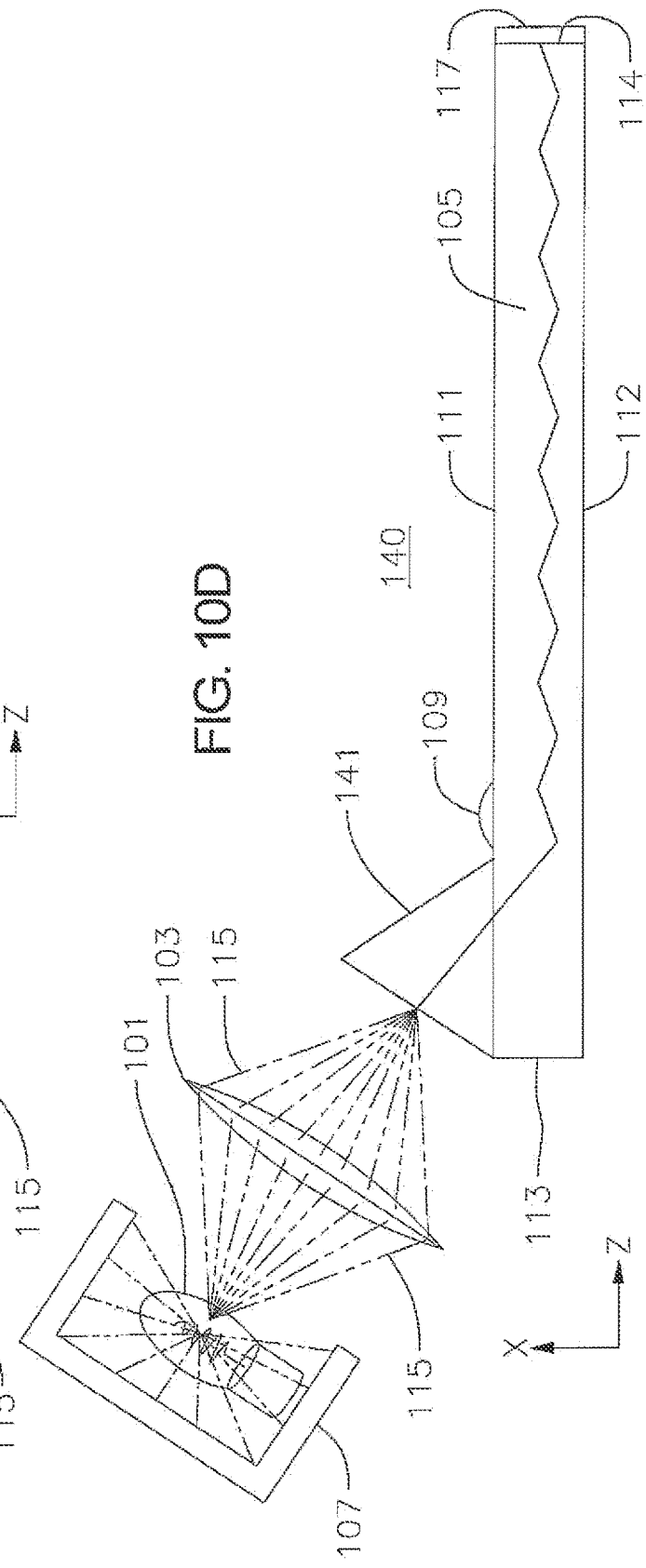

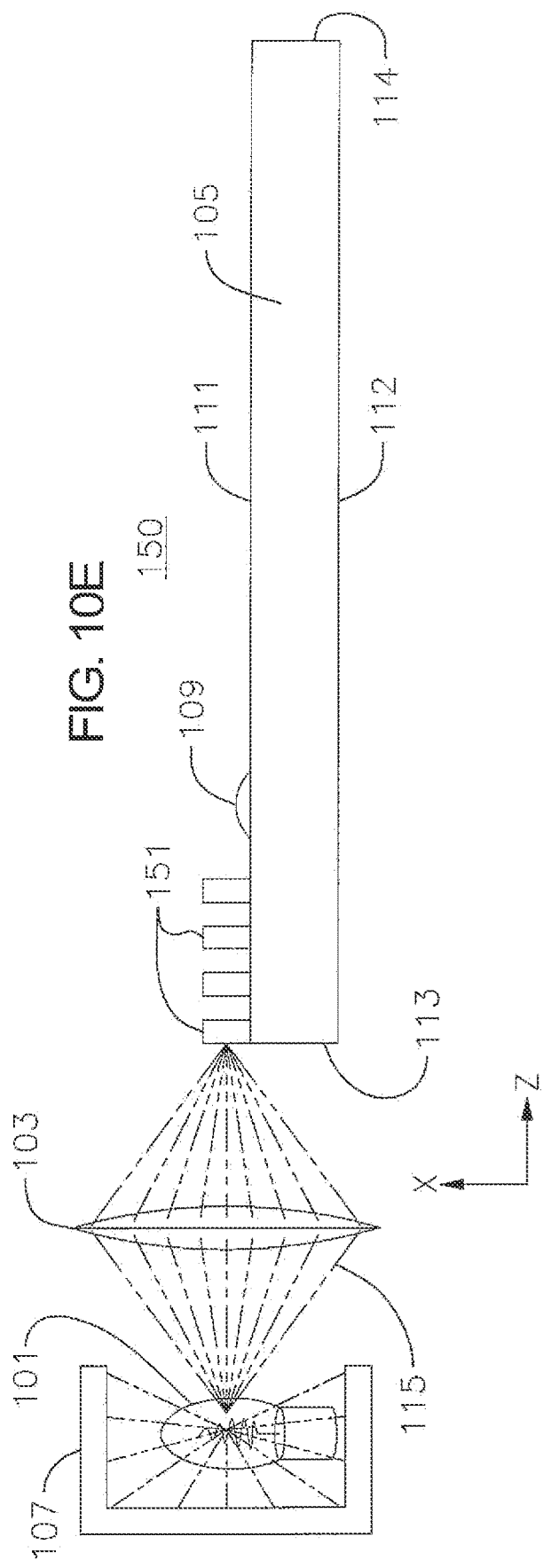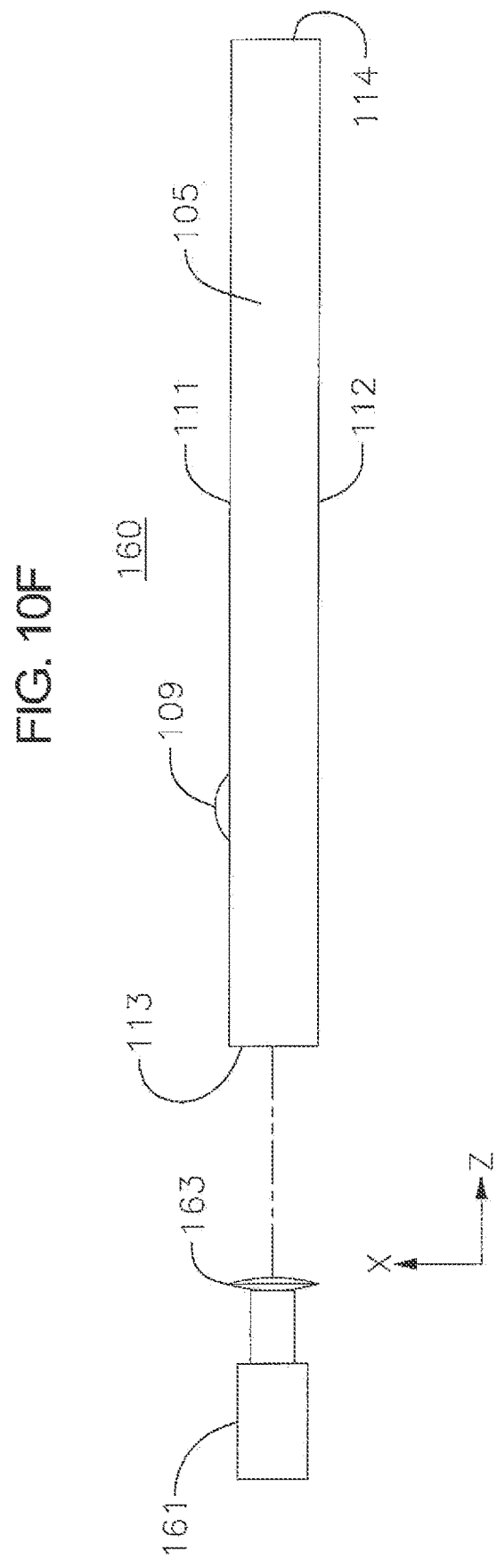

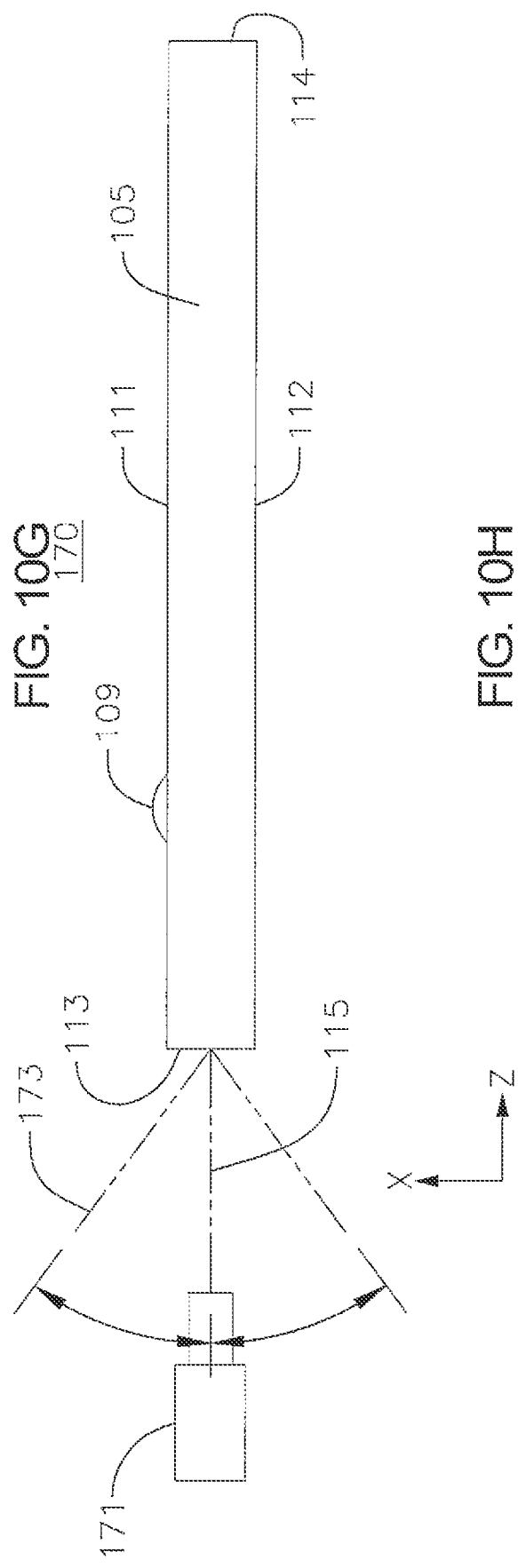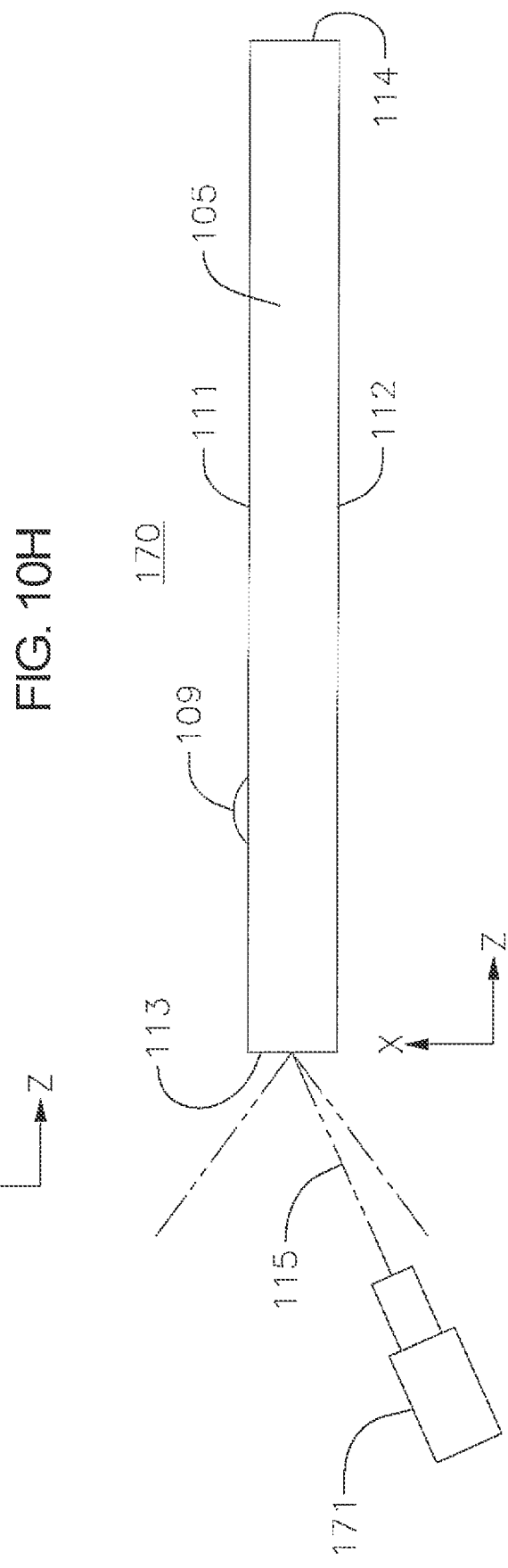

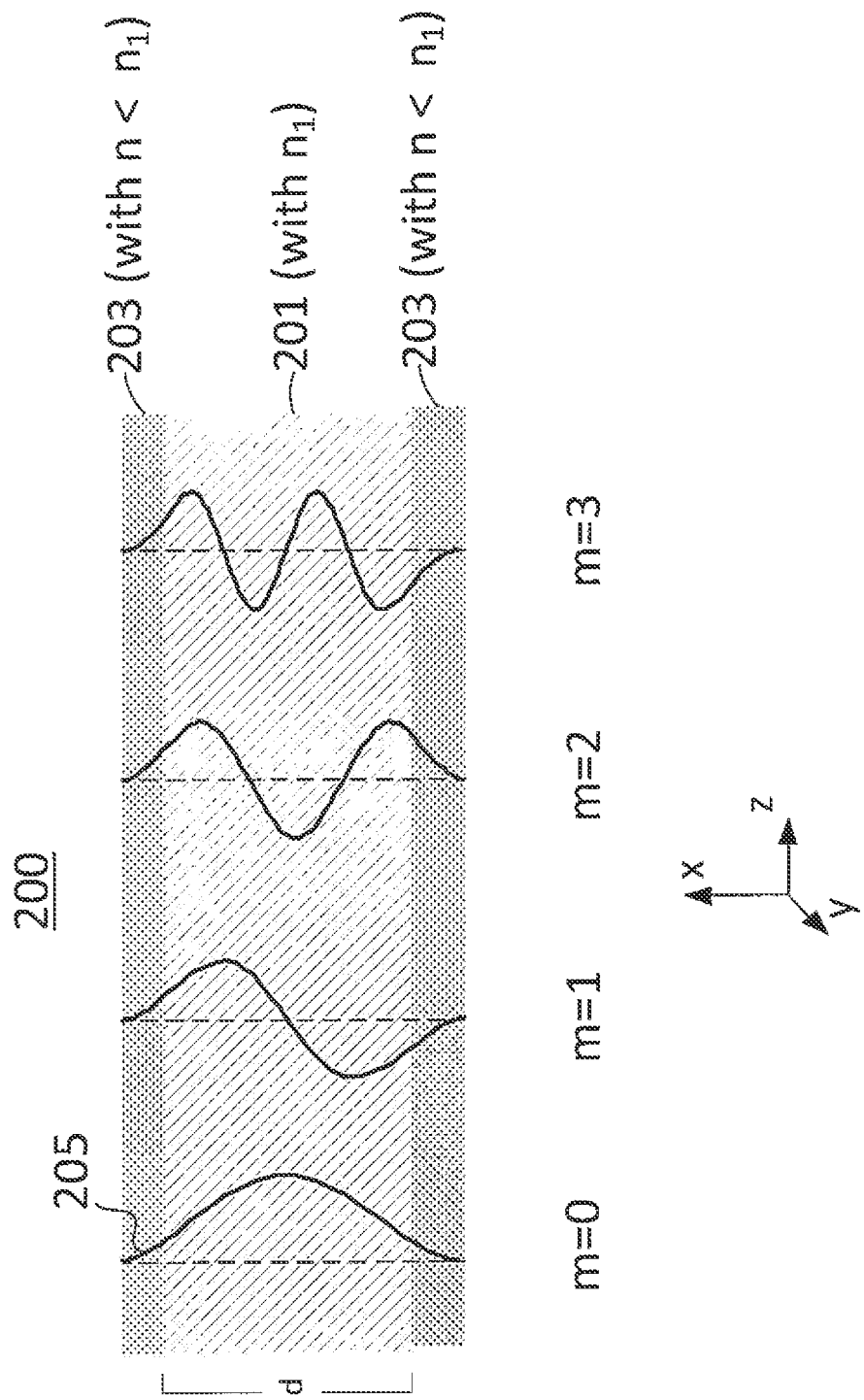

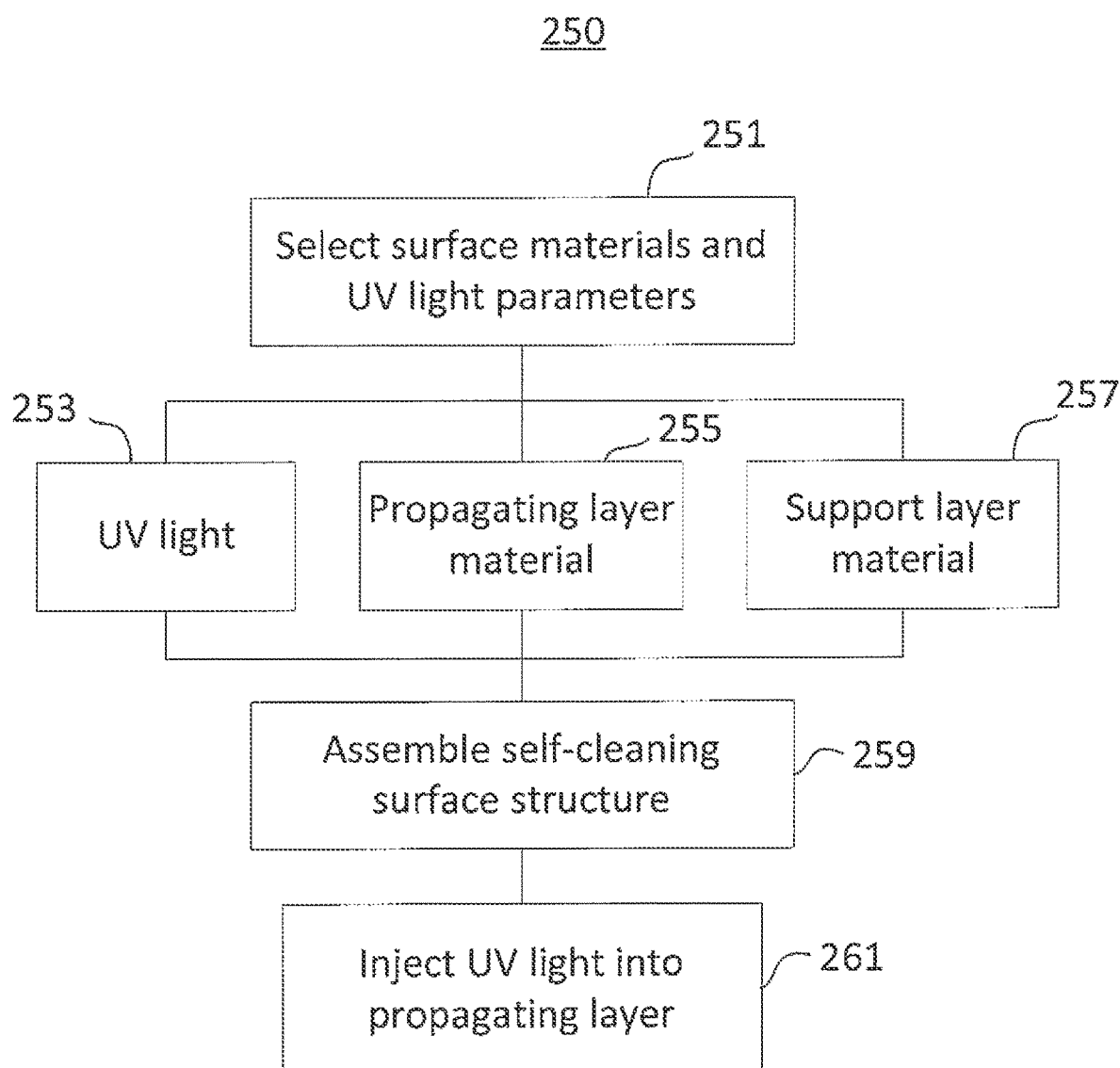

SELF-SANITIZING WAVEGUIDING SURFACES

CROSS-REFERENCE TO RELATED APPLICATION(S)

This application is divisional of U.S. patent application Ser. No. 17/036,474, filed Sep. 29, 2020, which is a divisional of U.S. patent application Ser. No. 15/870,082 filed Jan. 12, 2018, now U.S. Pat. No. 10,821,198, which claims priority to and the benefit of U.S. Provisional Patent Application No. 62/461,415 filed Feb. 21, 2017, the entire contents of all of which are incorporated herein by reference.

FIELD

The present disclosure relates generally to antimicrobial and self-sanitizing surfaces, and more specifically to an apparatus and/or surface structure that is cleaned with ultraviolet (UV) light.

BACKGROUND

Surfaces contaminated by pathogenic organisms such as bacteria, viruses, and/or fungi commonly act as vectors for the spread of such organisms between human hosts. Such contamination is a particular problem in high-traffic areas such as public bathrooms and facilities, food preparation environments such as factories and kitchens, shared vehicles such as transit, buses, rideshare, and taxis, and healthcare environments such as hospitals and ambulances, because these environments often come into contact with large numbers of people, contain numerous surfaces that may be difficult to clean, and/or may be repeatedly exposed to substances containing elevated loads of disease-causing pathogens. Managing such surface contamination in order to prevent or reduce cross-contamination and disease transmission is a crucial problem in public health. Accordingly, there is a need for technology that allows surfaces in such environments to be quickly and thoroughly sanitized.

One approach toward surfaces that can be thoroughly disinfected involves the use of antimicrobial chemicals on or within a surface. For example, coatings of silver (Ag) or quaternary ammonium polymers may be applied as a thin layer over the top of a contamination-prone surface such as a counter or doorknob. The materials in the coating disrupt the cell walls of any microbes that are in contact with the coating, thereby causing these microbes to die. However, the time required for such coatings to kill microbes is often on the order of several hours. Furthermore, the coatings wear off and lose efficacy over time, and must be periodically replaced. Similarly, antimicrobial and disinfecting chemical cleaners (such as those including surfactants, ethanol, and/or bleach) wear off quickly and must be repeatedly topically applied.

Another approach toward surfaces that can be quickly disinfected is to utilize ultraviolet (UV) light. For example, a UV light source may be permanently or temporarily suspended over a surface, such that UV light may be intermittently applied to that surface. When the UV light is incident on pathogens on that surface, the UV light induces oxidative damage of genetic material and proteins within those pathogens, thereby disrupting crucial biochemical pathways and triggering pathogen inactivation and/or cell death. The utilization of UV light has a significant advantage over antimicrobial coatings in its significantly shorter timescale required for pathogen destruction (i.e., seconds instead of hours). However, some frequencies of UV light can be detrimental to human health, and thus, their use in environments frequented by humans and other animals must be carefully controlled and monitored. Moreover, the UV light source must have high power in order to achieve an optical flux sufficient for killing microorganisms. Accordingly, improved strategies for managing surface contamination by pathogens are still needed.

SUMMARY

Aspects of embodiments of the present disclosure are directed toward a self-sanitizing surface structure (self-sanitizing waveguide surface), a method of fabricating a self-sanitizing surface structure, and a method of reducing contamination on a self-sanitizing surface structure.

Additional aspects will be set forth in part in the description which follows, and, in part, will be apparent from the description, or may be learned by practice of the presented embodiments.

According to embodiments of the present disclosure, a self-sanitizing surface structure may include a waveguide; the waveguide including: a propagating layer having a is first transverse side and a second transverse side opposite the first transverse side, the first transverse side being exposed to air and configured to selectively refract light; and a support layer in direct contact with the second transverse side of the propagating layer. The waveguide may be configured to selectively refract about 0.01% to about 25% of the flux of an ultraviolet (UV) light injected into the propagating layer, the selective refraction occurring when (for example, only when) a residue is on the first transverse side and at an interface with the residue.

The propagating layer in the self-sanitizing surface structure may be formed of amorphous silica, quartz, a metal fluoride, a fluoropolymer, a cyclic ether-containing fluoropolymer, a PTFE-terpolymer, polychlorotrifluoroethylene (PCTFE), a cyclic olefin copolymer (COC), polymethylpentene, or zinc sulfide.

The propagating layer in the self-sanitizing surface structure may have a refractive index of about 1.3 to about 2.5.

The support layer in the self-sanitizing surface structure may include a mirror or metallic layer.

The support layer in the self-sanitizing surface structure may have a lower refractive index than the propagating layer.

The support layer in the self-sanitizing surface structure may include a layer of air, porous silica (silicon), or a low refractive index metal fluoride.

The self-sanitizing surface structure may further include: an ultraviolet (UV) light source for generating UV light; and optics to direct the UV light into the propagating layer, the optics being directly coupled to an end of the propagating layer perpendicular to the first and second transverse sides.

The UV light source in the self-sanitizing surface structure may be an excimer lamp, a downshifting excimer lamp, an excimer laser, a light emitting diode (LED), a mercury (Hg) vapor lamp, or a light source comprising AlGaN quantum wells.

The UV light source in the self-sanitizing surface structure may generate UV-C light.

The optics included in the self-sanitizing surface structure may include collimating optics, mirrors, refractive or reflective lenses, metamaterial-based lenses, Fresnel lenses, fibers, standard single mode optical fibers, multimode optical fibers, photonic crystal optical fibers, or a combination thereof.

The optics included in the self-sanitizing surface structure may by coupled to the end of the propagating layer via a prism or grating.

The propagating layer in the self-sanitizing surface structure may not include any germicidal coating or layer on the first transverse side.

The self-sanitizing surface structure may further include a metal coating on the first transverse side of the propagating layer, the metal coating being configured to convert ultraviolet (UV)-C photons to surface plasmon polaritons (SPPs).

The self-sanitizing surface structure may further include an optical mirror on a terminating longitudinal side of the propagating layer.

The self-sanitizing surface structure may further include a structural layer under the support layer.

The waveguide in the self-sanitizing surface structure may be configured to support multimode waveguiding behavior.

The residue on the first transverse side of the waveguide may include an organic compound, a microorganism, or a nucleic acid.

The self-sanitizing surface structure may further include: an additional waveguide adjacent to the waveguide, the additional waveguide including a propagating layer; and parallel feeding optics or optics splitters to divide and inject the UV light into the propagating layers of the waveguide and the additional waveguide.

According to embodiments of the present disclosure, a method of fabricating the self-sanitizing surface structure of claim 1 may include: attaching optical mirrors to a substrate, the optical mirrors having a height larger than that of the substrate; forming the support layer on the substrate between the optical mirrors; forming the propagating layer by applying an ultraviolet (UV)-transparent pre-polymer coating on the support layer between the optical mirrors and curing the UV-transparent pre-polymer coating; and coupling a UV light source to an injection end of the propagating layer.

According to embodiments of the present disclosure, a method of reducing contamination on a self-sanitizing surface structure includes: selecting a wavelength of UV light and a light injection angle; selecting a material for a propagating layer and a material for a support layer; assembling the self-sanitizing surface structure from the selected material for the propagating layer and the selected material for the support layer to form a waveguide; and injecting UV light into the propagating layer at the light injection angle to selectively refract about 0.01% to about 25% of the flux of the UV light at a transverse side of the waveguide in the self-sanitizing surface, the selective refraction occurring when (for example, only when) a residue is on the waveguide and at an interface with the residue.

BRIEF DESCRIPTION OF THE DRAWINGS

These and other features and advantages of embodiments of the present disclosure will become more apparent by reference to the following detailed description when considered in conjunction with the following drawings, in which:

FIG. 3 is a schematic diagram illustrating injection of a light ray into a waveguide with respect to the acceptance angle of the waveguide, followed by total internal reflection and transmission through the waveguide;

FIG. 8 is a table listing the dissociation energies (in eV) and ultraviolet (UV) light wavelengths for dissociation (in nm) of some chemical bonds commonly found in organic and bioorganic residues, toxins, and chemical weapons, reproduced from Table 2.10 in Chapter 2 of Tsia, K. ed., *Understanding Biophotonics: Fundamentals, Advances, and Applications*, 2015, Taylor and Francis Group LLC, Boca Raton, FL, the entire content of which is incorporated herein by reference;

FIG. 9 is a series of tables listing the chemical bond dissociation energies (in kJ/mol) of selected phosphorus and nitrogen-containing chemical bonds, reproduced from the entry for "Bond Dissociation Energies" in Dean, J. A., *Lange's Handbook of Chemistry*, 15th ed., 1998, McGraw-Hill, New York, NY, the entire content of which is incorporated herein by reference;

FIGS. 10A-10H are schematic diagrams showing various example embodiments of optical components that may be connected to the propagating layer 105 of a self-sanitizing surface structure. FIG. 10A shows an example embodiment of a self-sanitizing surface structure in which the optics include a UV lamp (bulb), a mirror box surrounding the UV lamp, and a focusing lens. FIG. 10B shows an example embodiment of a self-sanitizing surface structure in which the optics include the same optics as in FIG. 10A, as well as a mirror on the terminal end of the propagating layer. FIG. 10C shows an example embodiment of a self-sanitizing surface structure in which the optics include a first focusing lens, and a second focusing lens. FIG. 10D shows an example embodiment of a self-sanitizing surface structure in which the optics include a prism. FIG. 10E shows an example embodiment of a self-sanitizing surface structure in which the optics include a diffraction grating. FIG. 10F shows an example embodiment of a self-sanitizing surface structure in which the optics include an LED laser with an integrated lens. FIGS. 10G and 10H show an example embodiment of a self-sanitizing surface structure 170 in which the optics include a led laser 171 without an integrated lens;

FIG. 11 is a schematic diagram illustrating the first four (lowest energy) modes of the transverse component of a light wave undergoing TIR and propagation within a waveguide including cladding along the sides perpendicular to the x-axis. The light waves are alternatingly of the form $\sin(\theta)$ and $\cos(\theta)$, where $\theta$ is constrained to $m\pi/d$, d is the distance between the sides of the waveguide, and m is an integer greater than or equal to 1. The energies associated with the light wave increase from left to right;

FIG. 13 is a flowchart summarizing the factors and acts included in the method of decontaminating or reducing residue contamination on a self-sanitizing surface structure utilizing selectively refracted light.

DETAILED DESCRIPTION

Figure 1A:
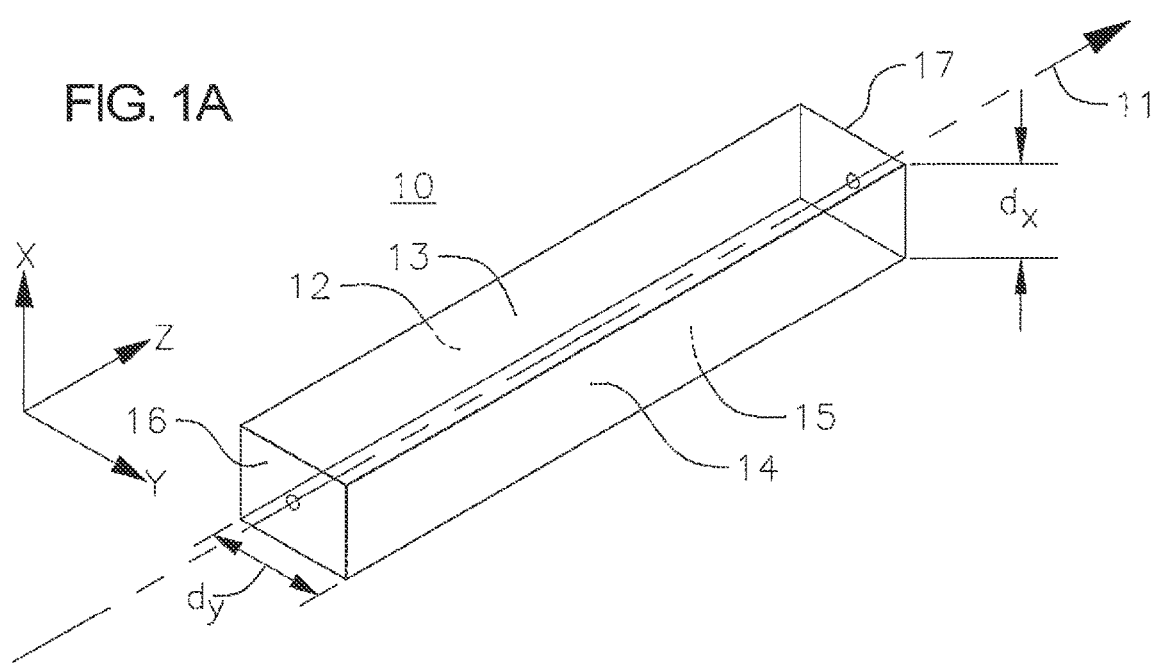
FIG. 1A is a schematic diagram showing the structure of a straight (planar) is example channel waveguide 10 extending in the z direction and being guided along the x and y directions.

In the following detailed description, only certain example embodiments of the subject matter of the present disclosure are shown and described, by way of illustration. As those skilled in the art would recognize, the subject matter of the present disclosure may be embodied in many different forms and should not be construed as being limited to the embodiments set forth herein.

In the context of the present application, when a first element is referred to as being "on", "coupled to", or "connected to" a second element, it can be directly on, directly coupled to, or directly connected to the second element, or can be indirectly on, indirectly coupled to, or indirectly connected to the second element with one or more intervening elements interposed therebetween. Like reference numerals designate like elements throughout the specification. The thicknesses of layers, films, panels, regions, etc., may be exaggerated in the drawings for clarity. The drawings are not necessarily drawn to scale.

As used herein, the terms "[to] clean", "cleaning", "[to] decontaminate", "decontaminating", and other verb form variations thereof may refer to the partial or full removal or destruction of substances that are harmful to human health, and more generally to the removal or destruction of substances that have the potential to cause harm, loss, or inconvenience. While it will be understood that the scope of such substances is not limited to any particular size, material, or amount, such cleaning and decontaminating action may be particularly useful for the removal of biologically and/or chemically harmful substances or residues that are not visible to the unaided human eye due to their particle size and/or amounts. Non-limiting examples of such substances may include biological agents, such as viruses, bacteria, fungi, protozoa, and other pathogenic microorganisms; peptides, proteins, deoxyribonucleic acid (DNA), and other nucleic acid sequences produced by such microorganisms, as well as chemical agents, including toxins, poisons, irritants, substances used in chemical warfare, and explosive materials. The terms may be used interchangeably with the terms "disinfecting", "sanitizing", "sterilizing", etc., particularly when the substances to be removed include biological agents. The term "self-sanitizing" refers to an ability of a surface to routinely and inherently remove such substances in the absence of physical labor, including application of a secondary substance and/or physical labor such as scrubbing, wiping, etc.

As used herein, the terms "contaminant" or "residue" may refer to, for example, any substance or material subject to removal or destruction during decontamination by embodiments of the present disclosure, including the pathogenic, biological, and/or chemical agents described above.

As used herein, the term "light" is used in its art-recognized sense to refer to electromagnetic radiation having any wavelength. For example, although the term encompasses visible light (e.g., light having a wavelength of 400-700 nm) as implied by the vernacular use of the term, it will be understood that references to "light" are not limited to visible light, and expressly include electromagnetic radiation having wavelengths outside of the visible range, including wavelengths corresponding to gamma rays, X-rays, ultraviolet (UV) rays, infrared waves, microwaves, radio waves, etc. Further, the term "light" may be used to refer to light including a single wavelength, as well as light including a mixture or range of wavelengths. In some embodiments, the term "light" may refer to electromagnetic radiation having a wavelength that is selected for a specific purpose, for example, its efficacy in terminating a specific organism or degrading a specific type of chemical bond.

In some embodiments, the term "light" may be used to specifically refer to ultraviolet (UV) radiation having a wavelength of 10 nm to 400 nm, including one or more wavelengths in the UV-A spectrum (e.g., about 315 nm to about 400 nm), the UV-B spectrum (e.g., about 280 nm to about 315 nm), the UV-C spectrum (e.g., about 200 nm to about 280 nm), and/or the vacuum UV (VUV) spectrum (e.g., about 10 nm to about 200 nm). In some embodiments, the term "light" may specifically refer to ultraviolet radiation including one or more wavelengths in the UV-C spectrum.

Furthermore, due to the dual wave-particle nature of electromagnetic radiation and light, it will be understood that although various descriptions of light herein may refer to "a ray", "a wave", "a photon", etc., such terms may be used interchangeably, and the utilization of any of these terms does not exclude the other terms, or models and formalisms using those terms.

As used herein, the terms "emit" and "emission" may be used to refer to light or other electromagnetic radiation being generated by and released from a light source, such as a UV lamp. The terms "refract" and "refraction" may be used to refer to light being transmitted across a phase boundary (e.g., a boundary between phases including unlike materials), and particularly to light exiting a surface or outer boundary of a waveguide, surface structure, or other structure that does not itself generate light, but is capable of internally transmitting light and releasing that light across the boundary under selected conditions. The term "transmit" and "transmission" may be used to refer to light moving both through a material and across a boundary, and in some cases, the situations may be distinguished by referring to, for example, "transmission through" or "within" a material and "transmission at" or "across" a boundary. However, in some cases the terms may be used interchangeably, and it will be understood that those having ordinary skill in the art are capable of distinguishing the origin and activity of the light according to context and the principles described herein.

The use of light (and particularly UV light) to kill microorganisms in the art has typically involved the use of bulky UV light source fixtures above the item or surface to be decontaminated. For example, such UV light may be generated by a mercury lamp, excimer lamp, or LED (e.g., UV-C LED) and transmitted through the air during application to the item or surface. However, the UV light is not selective for pathogenic organisms over other organisms, and the wavelengths and fluxes of UV light commonly used for this purpose are also capable of causing skin and eye damage to humans, including short-term damage such as tissue burns, and long-term damage such as accelerated cell aging and DNA mutagenesis associated with development of cancer. As such, UV-assisted decontamination has typically been limited to select environments with the help of strict control measures.

Aspects of embodiments of the present disclosure are directed toward a self-sanitizing surface structure (self-sanitizing waveguide surface), a method of fabricating a self-sanitizing surface structure, and a method of reducing contamination on a self-sanitizing surface structure. The self-sanitizing surface structure may be configured to selectively refract light having a wavelength suitable for destroying or reducing the concentration of residues on the self-sanitizing surface structure, and the method of reducing such contaminating residues may operate by selectively refracting light. Specifically, aspects of embodiments of the present disclosure are directed toward the utilization of a waveguide to guide, constrain, and selectively refract or transmit UV light from within a surface structure under specific conditions (e.g., only in the presence of a contaminating residue, and only at the interface between the self-sanitizing surface structure and contaminating residue), such that contamination can be reduced on the outside of the surface structure with a decreased risk of human exposure to the UV light. Furthermore, some embodiments of the self-sanitizing surface structure may prevent or limit refraction or transmission of UV light from within the surface structure where the structure is in direct contact with a vacuum or gas (e.g., in areas of the surface where residue is not present and the surface is exposed to air and/or the environment adjacent to the structure).

The term "surface structure", as used herein, may refer to a layer of material on or forming the outside or outermost part of an object. The "surface structure" may be a layer having a defined thickness and volume, and in some embodiments, may be applied to or cover the outside of an object made of materials different from those included in the surface structure layer. For example, a conformal layer applied to the flat upper face of a countertop or the grasped portion of a rounded doorknob may be referred to as a "surface structure".

The term "surface", when used without the following noun, is used in its geometrically understood sense to refer to the two-dimensional area or manifold defining a boundary of a three-dimensional layer, object, or space. Throughout this specification, planar areas corresponding to surfaces of a surface structure may be distinguished from the surface structure itself by instead or additionally being referred to as "sides" (e.g., an upper side, a lower side) or "boundaries" (e.g., an upper boundary, a lower boundary) of the surface structure. Planar or two-dimensional areas corresponding to a boundary between two different named materials may be additionally or specifically referred to as "interfaces". When orientation and positional descriptors are used to distinguish between various sides of a surface structure (e.g., upper side, lower side, left side, right side), such descriptors may be interpreted with reference to the example embodiments described in the accompanying drawings. However, it will be understood that embodiments of the present disclosure are not limited to the orientations depicted in the drawings. For example, although example embodiments may be described herein as being oriented so that residues are deposited on and light is refracted at an "upper side" with respect to the waveguide included in the self-sanitizing surface structure, the self-sanitizing surface structure may be rotated or reoriented so that the "upper side" of the waveguide faces a different direction with respect to gravity. For example, while some drawings may depict a self-sanitizing surface structure attached to the upper-facing surface of a countertop, additional examples in which a self-sanitizing surface structure is attached to, e.g., the downward-facing surface of a ceiling or a side-facing surface of a wall are also included within the scope of embodiments of the present disclosure.

The term "selectively refract", as used herein, indicates that light refracted by the self-sanitizing surface structure is not continuously refracted (i.e., not continuously released from the surface). Rather, the surface structure is designed and configured so that light is refracted only under specific conditions and in a controlled manner with respect to time and space. In some embodiments, the surface structure may be configured so that light is substantially contained within the surface structure under initial conditions (e.g., in air), but is refracted outside of the structure only in the presence of a non-air residue, for example, a residue having a refractive index higher than that of air. Furthermore, when light is refracted in the presence of such a residue, light is refracted only at the portion of the surface structure that is directly adjacent to or in direct contact with the residue. As such, the refraction of light is not uniform across the surface structure, but instead exhibits spatial and temporal variations based on the specific configuration of the surface structure in contact with the environment. Further, refraction can be automatically triggered by environmental conditions, rather than requiring user monitoring and/or intervention.

As used herein, the term "waveguide" is used in its art-recognized sense to refer to a structure configured to guide or constrain the transmission of waves (such as electromagnetic waves), such that the waves propagate only within the space and along the direction traversed by the waveguide. In the absence of a waveguide, a wave propagates from a point source through open space (e.g., in all directions) as a three-dimensional (e.g., spherical) wave. Further, the power (i.e., intensity) of the spherical wave decreases by a factor of $1/r^2$ with increasing radial distance r from the wave source, which can be understood as a decrease in flux density as the surface area of the spherical wavefront increases. However, a waveguide constrains waves held within that structure to propagate in a reduced number of dimensions (i.e., one or two). As a result, the flux density in the planar (two-dimensional) or one-dimensional wavefront decreases at a much slower rate. In the case of a channel waveguide, the power of the wave ideally remains constant throughout propagation (e.g., assuming zero losses due to coupling and physical interactions such as scattering with and within the constituent materials).

When a wave is guided or constrained with respect to a particular dimension (direction), that dimension may be referred to as a "dimension of guidance".

The terms "channel structure waveguide" and "channel waveguide" may be interchangeably used herein to refer to a waveguide in which a wave is guided (i.e., constrained) along two dimensions, and propagates freely along one dimension or direction (e.g., as a 1D wave). For example, a channel waveguide may be elongated in the z direction relative to the x and y directions. The structure or form of a channel waveguide may be understood by analogy to an aqueduct (i.e. a channel for water having a length much longer than its height and width). In a channel waveguide, the four transverse sides of the waveguide extend substantially parallel to the overall direction of wave propagation and the normal vectors of those sides are substantially perpendicular to the overall direction of wave propagation. As used herein, the term "overall direction of wave propagation" refers to the vector describing the overall movement (momentum) of a light wave transmitted directly down the center of the waveguide.

The terms "slab waveguide", "planar waveguide", and "slab structure waveguide", etc., are interchangeably used to refer to a waveguide in which a wave is guided (e.g., constrained) along one dimension, and propagates freely along two dimensions (e.g., as a 2D wave in a plane). For example, a slab waveguide may be elongated in the z and y directions relative to the x direction. In a slab waveguide, the two transverse sides of a waveguide extend substantially parallel to the plane of wave propagation and the normal vectors of those sides are perpendicular to the plane or overall direction(s) of wave propagation.

In both types or kinds of waveguide structures, the longitudinal side(s) refers to the remaining, non-transverse sides of the waveguide. In some embodiments, the longitudinal sides of a waveguide are oriented with respect to the transverse sides of the waveguide at an angle of 90°, such that those sides have normal vectors that are substantially parallel to the overall direction(s) of propagation. However, embodiments of the present disclosure are not limited thereto. In some embodiments, the longitudinal sides of the waveguide, channel waveguide, and/or slab waveguide may be sloped (e.g., may be oriented with respect to the transverse sides of the waveguide at an angle other than 90°, such that, for example, a cross-section of the waveguide has the shape of a trapezoid, parallelogram, etc.). In some embodiments, the transverse sides of the waveguide may be curved.

FIG. 1A is a schematic diagram showing the structure of a straight (planar) example channel waveguide 10 extending in the z direction and being guided along the x and y directions. The overall direction of light wave propagation is substantially along the direction of the wave vector arrow 11. The four transverse sides 12, 14, 13, and 15 of the channel waveguide 10 substantially extend along the z direction and along the direction of wave propagation, and may also be defined by their normals, which are substantially perpendicular to the wave vector arrow 11. The two longitudinal sides 16 and 17 of the channel waveguide 10 may be defined as being substantially normal to the wave vector arrow 11. Although the example channel waveguide 10 depicted in FIG. 1A is substantially planar, embodiments of the present disclosure are not limited thereto, as described below.

Figure 1B:
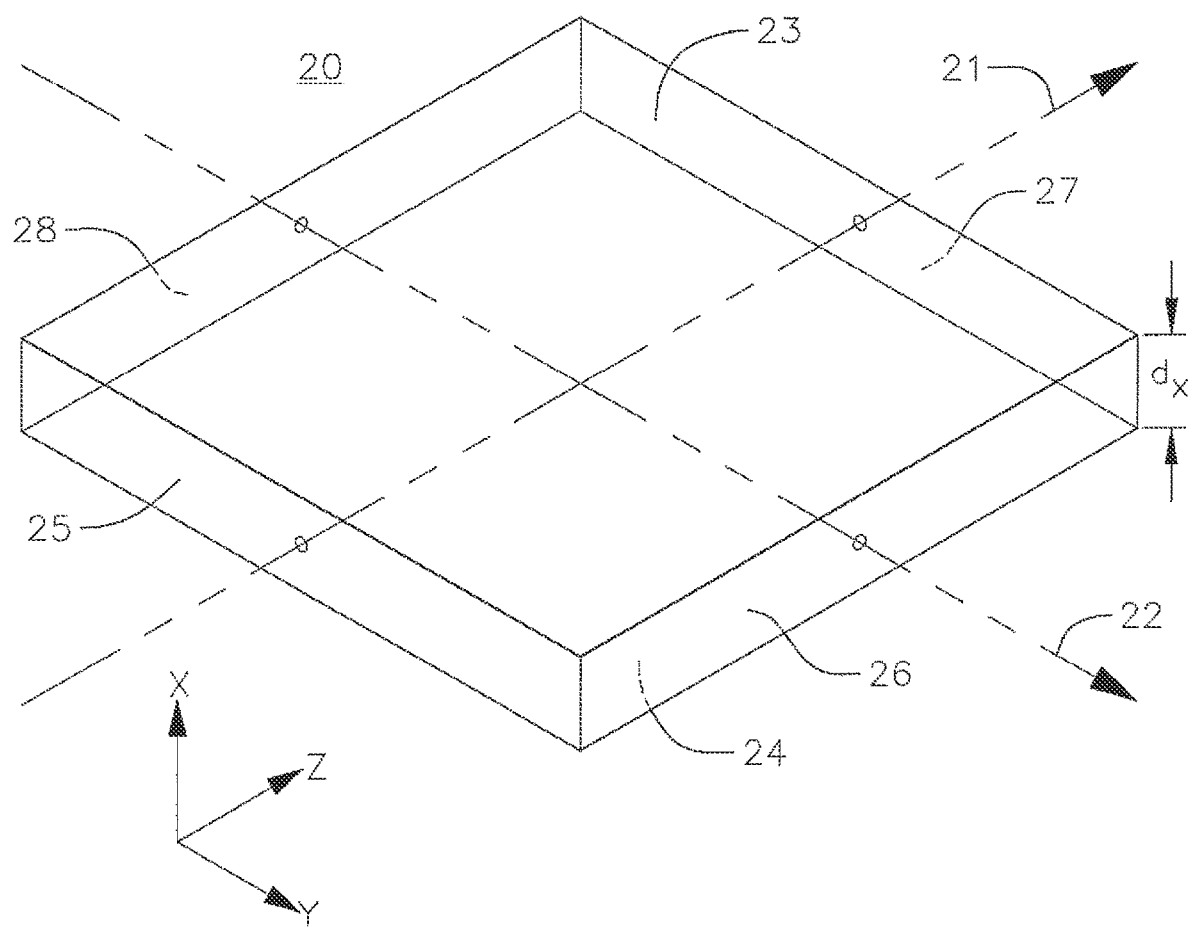
FIG. 1B is a schematic diagram showing the structure of a straight (planar) example slab waveguide 20 extending in the y and z directions and being guided along the x direction.

FIG. 1B is a schematic diagram showing the structure of a straight (planar) example slab waveguide 20 extending in the y and z directions and being guided along the x direction. The overall direction of light wave propagation is substantially along the direction of the two wave vector arrows 21 and 22 (e.g., as a 2D wave in the y-z plane). The two transverse sides 23 and 24 of the slab waveguide 20 are substantially parallel to the y-z plane and have normals that are substantially perpendicular to the direction of wave propagation. The four longitudinal sides 25, 26, 27, and 28 of the slab waveguide 20 may be defined as being parallel to the direction of wave propagation. Although the example slab waveguide 20 depicted in FIG. 1B is substantially planar, embodiments of the present disclosure are not limited thereto, as described below.

In some embodiments, the waveguide, channel waveguide, and/or slab waveguide may be substantially flat or planar, as described above and/or as may be ascertained from the planarity of the transverse surfaces. In some embodiments, at least some portions of the waveguide, channel waveguide, and/or slab waveguide may be formed or bent to include a curvature or curved (non-planar) geometry, as may be ascertained from the non-planarity of the transverse surfaces. In these non-planar embodiments, a set of vectors describing the overall movement (momentum) of a light wave transmitted directly down the center of the waveguide may vary in direction at different coordinates along the waveguide, but should still describe a overall continuous field. As such, the terms "longitudinal sides" and "transverse sides", in the context of curved or non-planar waveguides, may still be used to identify or refer to the surfaces of the waveguide when considered with respect to the local directionality of the vector field.

In some embodiments, the waveguides referred to herein may be dielectric waveguides. The term "dielectric waveguide", as used herein, refers to a type or kind of waveguide that is formed by combining a light-transmitting propagating layer with light-transmitting surrounding materials (described below), such that the surrounding materials are placed along the dimensions of guidance. For example, a channel waveguide may include a propagating layer that is substantially elongated in the z direction (with respect to the x and y directions), and is surrounded by the surrounding materials on its +x, −x, +y, and −y sides. A slab waveguide may include a propagating layer that is substantially elongated in the z and y directions (with respect to the x direction), and is surrounded by the surrounding materials on its +x and −x sides. The materials for the propagating layer and the surrounding materials may be selected in tandem, so that under specific conditions described herein, waves inserted into the propagating layer do not exit the propagating layer at interfaces between the propagating layer and the surrounding materials, but are instead reflected back into the propagating layer.

Because the surrounding materials included in a dielectric waveguide are capable of transmitting light, they can be described in terms of their refractive indexes. As used herein, the refractive index n (or index of refraction n) of a material is a dimensionless quantity that describes the extent to which the phase velocity of light is changed as it passes through that material with respect to a reference material (herein, air at standardized pressure, having a normalized refractive index of 1.0). For example, the refractive index of a material corresponds to the ratio of the speed of light in the reference material vs. the speed of light in the material of interest. As such, most refractive indexes are greater than 1 (i.e., the phase velocity of light is reduced in most materials). It will be understood that because the refractive index of a material varies according to the wavelength and frequency of light (which is the principle that causes light dispersion), the refractive indexes used and described herein are to be considered "effective refractive indexes" for the particular wavelength or range of wavelengths being used in the embodiment.

Residues on the surface of the waveguides included in self-sanitizing surface structure embodiments of the present disclosure may be selectively exposed to light transmitted within the waveguide via one or more mechanisms.

As a first exposure mechanism, in some embodiments, the residue may be exposed to light via refraction of light at the surface of the waveguide. In general, when light is incident on a planar interface between two materials having different refractive indexes, a portion of the light is reflected, and a portion of the light is transmitted or refracted (bent) at that interface. Using approximations associated with geometrical (ray) optics, the trajectory of the reflected portion can be described according to Equation 1:

$$\theta_i = \theta_r \qquad \text{Equation 1}$$

where $\theta_i$ is the angle of incident light with respect to the vector normal to that interface, and $\theta_r$ is the angle of reflected light with respect to the vector normal to that interface.

Figure 2A:
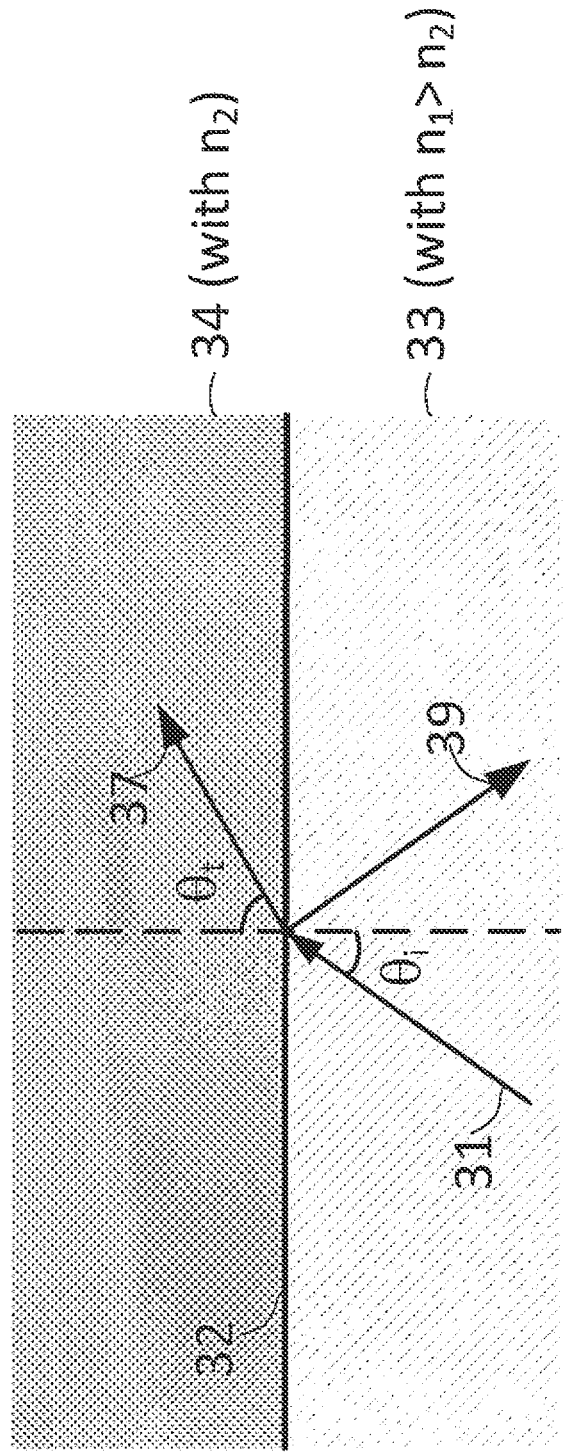
FIG. 2A is a schematic diagram illustrating the reflection and refraction of a ray of light at an interface between a first material (having a refractive index $n_1$) and a second material (having a refractive index $n_2$ smaller than that of the first material), as described by Snell's law (Equation 2), $n_1 \sin \theta_i = n_2 \sin \theta_t$.

Meanwhile, the trajectory of the refracted portion can be described according to Snell's law (Equation 2):

$$n_1 \sin \theta_i = n_2 \sin \theta_t \qquad \text{Equation 2}$$

where $n_1$ is the refractive index of the first material (i.e., the material before the interface), $n_2$ is the refractive index of the second material (i.e., the material after the interface), $\theta_i$ is the angle of incident light with respect to the vector normal (perpendicular) to that interface, and $\theta_t$ is the angle of transmitted light with respect to the vector normal to that interface. When $n_1 > n_2$, the resulting $\theta_t$ is larger than $\theta_i$ (i.e., the transmitted light is bent further away from the normal). FIG. 2A is a schematic diagram illustrating the reflection and transmission (refraction) of a ray of light 31 at an interface 32 between a first material 33 and a second material 34, specifically when the second material 34 has a refractive index smaller than that of the first material 33 and as described according to the variables in Equation 2. The relative amounts (i.e. intensities) of the transmitted (refracted) portion 37 and reflected portion 39 depend on the transmission and reflection coefficients for the interface. It will be understood that those having ordinary skill in the art are capable of calculating these coefficients from the refractive indexes of the first and second materials, if desired, but they are not crucial to the operation of embodiments of the present disclosure. The angle between the ray of light 31 and the normal to the interface is referred to as angle of incident light $\theta_i$ (35), while the angle between the transmitted (refracted) ray of light 37 and the normal to the interface is referred to as angle of transmitted light $\theta_t$(36).

Figure 2B:
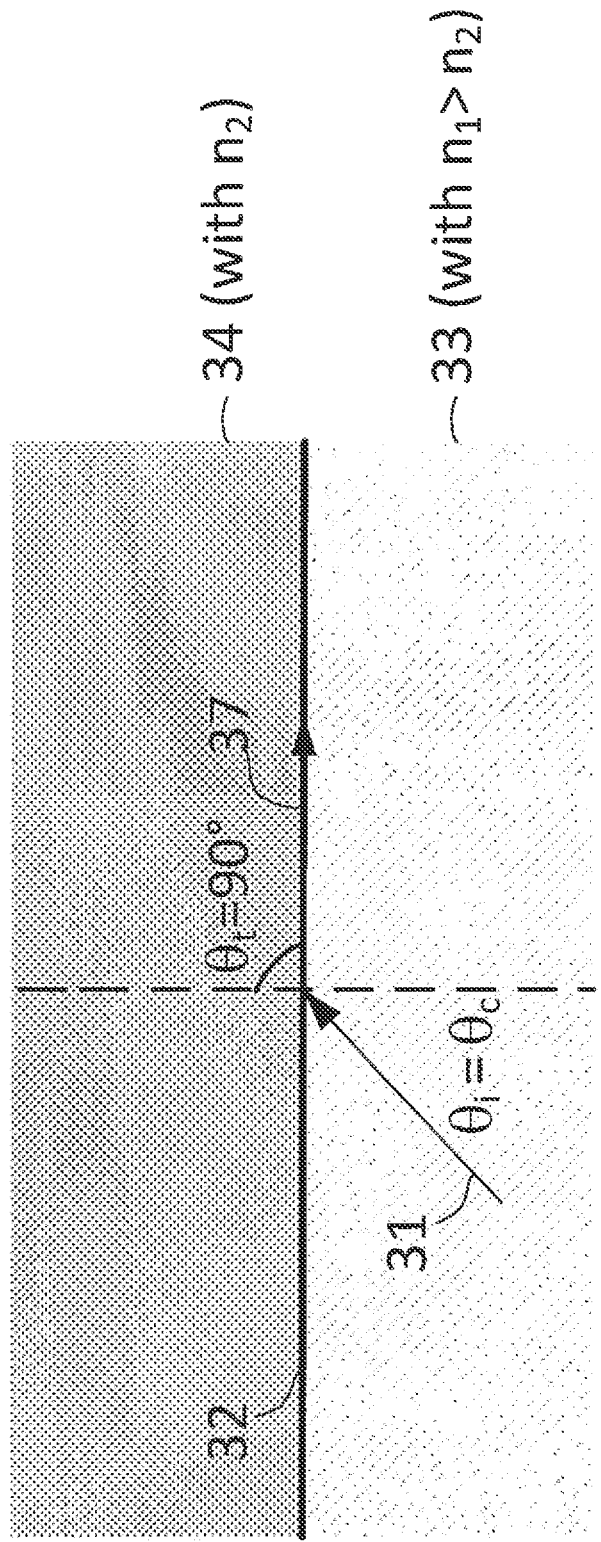
FIG. 2B is a schematic diagram illustrating the refraction of a ray of light at an interface between a first material (having a refractive index $n_1$) and a second material (having a refractive index $n_2$ smaller than that of the first material) in the case where $n_1$, $n_2$, and the angle of incidence $\theta_1$ are selected so that the angle of transmission $\theta_t$ is 90°.

For any given combination of $n_1$ and $n_2$ where $n_1 > n_2$, there exists an angle of incident light $\theta_i$ at which the resulting angle of transmitted light $\theta_t$ will be $\pi/2$ (90°). At this angle, the light is transmitted parallel to the interface between the two materials. FIG. 2B is a schematic diagram illustrating the refraction of a ray of light 31 at an interface 32 between a first material 33 and a second material 34, specifically when $n_1$, $n_2$, and 61 are selected so that $\theta_t$ (36) is 90°. The angle of incident light $\theta_i$ (35) that satisfies this condition is known as the "critical angle" $\theta_c$ (39), and is denoted by the dotted line 38. The critical angle may be further defined or calculated as $\theta_c = \arcsin(n_2/n_1)$.

Figure 2C:
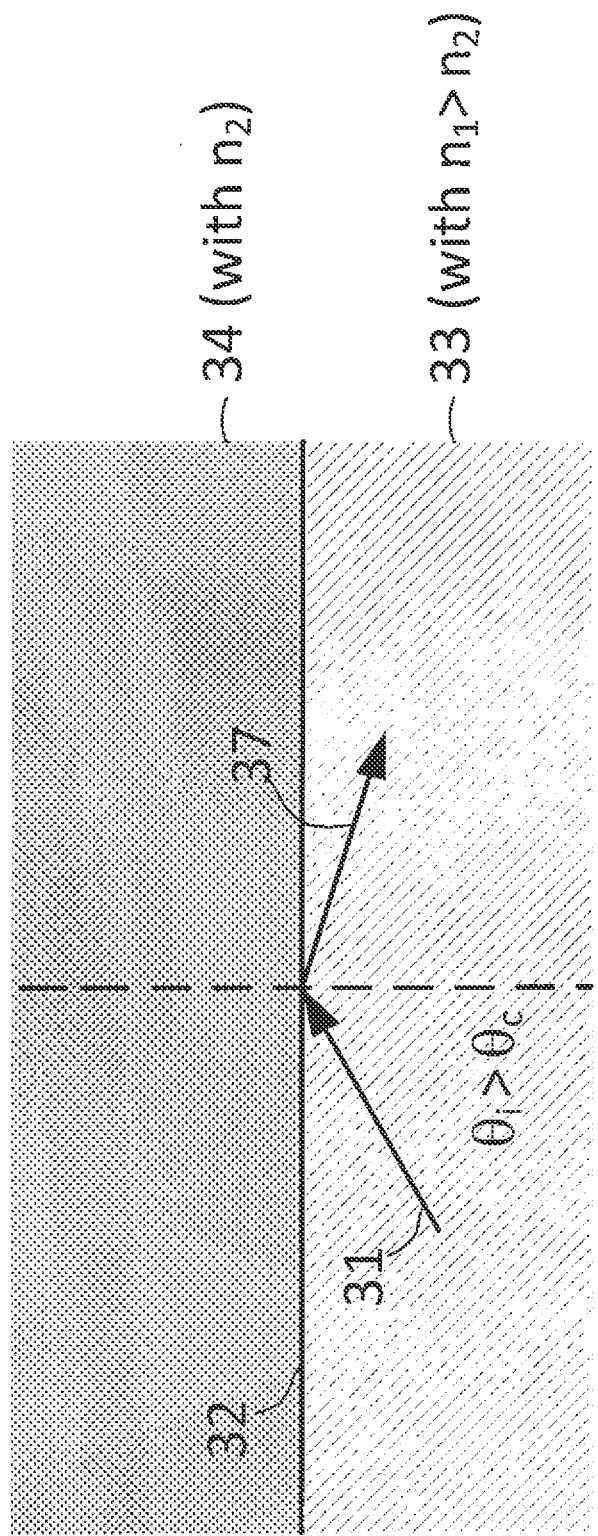
FIG. 2C is a schematic diagram illustrating total internal reflection (TIR) of a ray of light at the interface between the first material (having a refractive index $n_1$) and the second material (having a refractive index $n_2$ smaller than that of the first material) in the case where $\theta_i$ is equal to or greater than the critical angle $\theta_c$ (calculated as $\arcsin(n_2/n_1)$.

When the angle of incident light θ1 (35) is equal to or larger than the critical angle $\theta_c$ (39) (i.e., $\theta_c \leq \theta_i < 90°$), the resulting angle of transmitted light $\theta_t$ (36) is greater than or equal to 90° from the normal vector (i.e., $90° \leq \theta_t < 180°$). As such, the transmitted light is no longer transmitted and refracted past the interface of the two materials, but is instead reflected at the interface so that the light remains in the first material. In this special case, because all of the light is reflected at the interface according to the geometrical optics formalism, "total internal reflection" (TIR) is observed. FIG. 2C is a schematic diagram illustrating the total internal reflection of a ray of light 31 at an interface 32 between a first material 33 and a second material 34, specifically when $n_1 > n_2$ and $\theta_i$ (35) is equal to or greater than $\theta_c$ (39) (denoted by the dotted line 38). When these conditions regarding the critical angle are found on two or more sides of the waveguide, such that TIR occurs at each interface of the waveguide, the wave may continue to propagate down the length of the waveguide. In some embodiments, when the surrounding materials are solid (as opposed to being a liquid or gas), the materials may be referred to as "cladding" or a "cladding layer".

As can be understood from the above discussion of critical angle, the behavior of light within a waveguide is strongly dependent on the geometry with which light is initially injected or inserted into the waveguide. Accordingly, a waveguide may also be configured and described in terms of its acceptance angle. As used herein, the term "acceptance angle" is used in its art-recognized sense to refer to the largest angle, with respect to the core axis of the waveguide (e.g., the axis along which light is propagated by the waveguide), at which light may be injected into the waveguide and be subject to guidance, for example, via TIR. The light may be injected into the waveguide at a longitudinal edge of the waveguide that is not covered with a reflective material, cladding, etc. FIG. 3 is a schematic diagram illustrating injection of a light ray 31 into a waveguide 40 including a propagating layer 41 surrounded by cladding 42 (including but not necessarily air) in the +x and −x directions. When the ray of light 31 is injected into the propagating layer 41 along the z direction and at an angle equal to or smaller than the acceptance angle 44, the ray 31 subsequently hits the interface 45 between the propagating layer 41 and cladding 42 at an angle 35 equal to or larger than the critical angle 39 of that interface, such that the ray of light 31 is reflected back into the propagating layer 41. As the ray of light 31 travels back and forth between opposite sides of the waveguide 40, the light continues to be incident on each interface at an angle larger than the critical angle, thereby remaining constrained within the propagating layer 41 while being propagated in the z-direction. In contrast, a light ray that is injected into the waveguide at an angle larger than the acceptance angle 44 will not be reflected, and will leak out of the waveguide.

The acceptance angle $\theta_{ac}$ of a waveguide may be described or calculated according to Equation 3:

$$\sin \theta_{ac} = (n_1^2 - n_2^2)^{1/2} \qquad \text{Equation 3}$$

where $\theta_{ac}$ is the angle of light injection with respect to the axis of waveguide transmission (in FIG. 3, the z-axis), $n_1$ is the refractive index of the propagating material, and $n_2$ is the refractive index of the material surrounding the waveguide (e.g., cladding, liquid, or air). The "acceptance cone" circumscribed by the range of $\theta_{ac}$ rotated around the normal defines the range of injection angles at which the light will be constrained within the waveguide. As can be seen in Equation 3, the size (e.g., angle) of the cone is a function of the refractive indexes of the propagating material and the cladding or surrounding material, with larger cones enabled by larger differences in refractive index.

The waveguide may be configured so that under normal conditions, i.e., when the residue is not present, light propagating within the waveguide is contained within that structure (e.g., more than about 98%, 95%, 90%, 80% or 70% of the light flux is contained and is not refracted or transmitted through the surface of the waveguide). For example, the refractive index of the waveguide and the light injection angle may be selected as described in detail according to embodiments herein so that light propagating through the waveguide undergoes TIR when the residue is not present. When a residue is present on a surface of the waveguide, light may be refracted at the surface of the waveguide according to one or more mechanisms described below.

In some embodiments, when the residue is capable of transmitting light (e.g., the residue includes or is suspended in a solvent such as water, as in the case of a microorganism, biofilm, sneeze droplets, etc.), a dielectric interface different from that normally present in the waveguide (e.g., between the waveguide and air) may be formed. As such, the critical angle for internal reflection will be changed at the residue-waveguide interface. Specifically, when the residue has a refractive index higher than that of air (n=1.00), the critical angle for internal reflection within the waveguide surface at that specific portion or area of the interface will be increased relative to the portions of the waveguide surface that remain in contact with air.

For example, when the propagating material of the waveguide has a refractive index $n_1$=1.40 and is in contact with air ($n_2$=1.00), the critical angle $\theta_c$ for light in the waveguide material can be calculated using Snell's law (Equation 2) to be arcsin (1.00/1.40)=45.5°. Therefore, as described above, light incident on the air-waveguide interface will exhibit total internal reflection (TIR) when the angle of incidence $\theta_i$ is greater than or equal to 45.5° (e.g., $\theta_i \geq 45.5°$). However, when a residue containing mostly water ($n_{con}$=1.33) is deposited on the surface, the critical angle at the point of deposition increases to arcsin(1.33/1.40)=71.8°, and light incident on the air-waveguide interface will exhibit TIR only when the angle of incidence $\theta_i$ is greater than or equal to 71.8°. As such, light having an angle of incidence between 45.5° and 71.8° is trapped within the waveguide under clean or normal conditions (i.e., when the waveguide is in contact with air), but is refracted when the water-containing residue is present at the surface of the waveguide. Once refracted, the light can decontaminate the surface at the point of contact with the residue.

Figure 4:
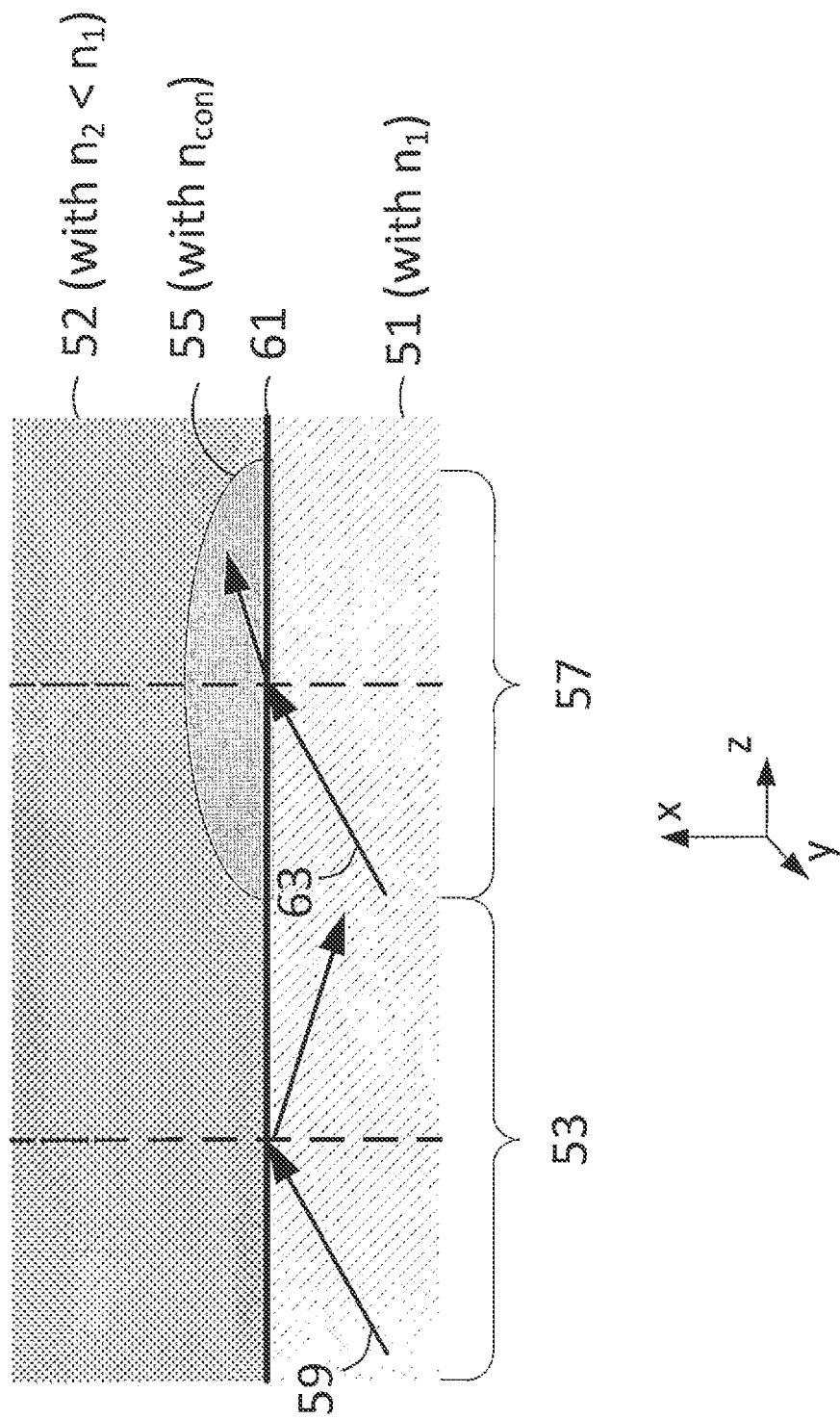
FIG. 4 is a schematic diagram illustrating an example embodiment in which a residue on a surface of a waveguide and having a refractive index $n_{con}$ larger than that of air ($n_2$=1.0) is exposed to light refracted at the surface of the waveguide due to changes in the condition ($\theta_c = \arcsin(n_2/n_1)$) for total internal reflection.

FIG. 4 is a schematic diagram illustrating an example of the above-described working principle. A "countertop" waveguide surface structure 51 having a refractive index $n_1$ is placed in direct contact with air ($n_2$<$n_1$) 52 in a first region 53 and with a water-containing residue 55 ($n_2$<$n_{con}$<$n_1$) in a second region 57. A first ray of light 59 incident on the interface 61 between the waveguide surface structure 51 and air 52 undergoes total internal reflection in the first region 53, while a second ray of light θ3 having the same angle of incidence is refracted at the interface 61 between the waveguide surface structure 51 and residue 55 in the second region 57. Accordingly, light may be contained in the first region and selectively refracted in the second region without requiring any modification to the waveguide or input from an operator.

When a residue with a refractive index similar to or substantially equal to that of the waveguide (i.e., the propagating layer of the waveguide) is deposited on the surface structure (e.g., $n_{con} \approx n_1$), the refractive index conditions for TIR are removed, and light is refracted at the surface (transmitted past the interface) regardless of the angle of incidence.

Changes in the ability of the waveguide to constrain light refraction can also be described in terms of changes in the acceptance angle $\theta_{ac}$ (i.e., the geometry of light injection) rather than the critical angle $\theta_c$. Specifically, when a residue having a refractive index higher than that of air (n=1.00) is present, $\theta_{ac}$ of the waveguide will be decreased relative to the clean waveguide. For example, a clean waveguide with $n_1$=1.40 and $n_2$=1.00 (as used in the example above) can be calculated via Equation 3 to have an acceptance angle of arcsin[$(1.96-1.00)^{0.5}$]=78.5°. In comparison, a waveguide with a residue deposited at any point along its side has a resulting acceptance angle of arcsin[$(1.96-1.77)^{0.5}$]=25.8°. As such, injected light having an acceptance angle between 25.8° to 78.5° is refracted at the point of contamination when a residue is present, but is constrained within the waveguide at all other points and/or when no residues are present.

As a second exposure mechanism, in some embodiments, the residue may be exposed to light in the form of evanescent waves. As used herein, the term "evanescent wave" may be used interchangeably with the term "surface wave" to refer to light that does not propagate sinusoidally through space (e.g., away from the surface) in the manner of other light waves or rays. Instead, the energy of the wave is concentrated within a short distance from the surface of the waveguide. Such evanescent waves are generated when the propagating light wave within the dielectric waveguide exhibits TIR, and can be understood as a consequence of the boundary conditions expressed in Maxwell's equations, which require electromagnetic waves to be continuous across dielectric interfaces. The field strengths (e.g., intensities) of such evanescent waves decrease (or decay) exponentially with increasing distance from the surface, such that the risk of unwanted exposure to the light also decreases to zero with increasing distance from the surface.

The evanescent waves may have a decay length or penetration distance (e.g., may extend from the surface to a distance) substantially equivalent to its lie roll-off point. The penetration distance d may be calculated according to Equation 4:

$$d = \lambda_0 / 2\pi n_1 [\sin^2\theta_1 - (n_2/n_1)^2]^{-1/2} \qquad \text{Equation 4}$$

wherein $\lambda_0$ refers to the wavelength of transmitted light, $n_1$ and $n_2$ refer to the refractive indexes of the waveguide and the surrounding material, respectively, and $\theta_1$ refers to the angle of incident light, as above. Equation 4 thus quantifies the relationship between the evanescent wave penetration distance and those variables, and demonstrates that the penetration distance may be tuned by selecting appropriate parameters.

For example, in a waveguide having $n_1$=2.0 that is in contact with a residue having $n_{con}$=1.5 but otherwise surrounded by air ($n_{air}$=1.0) may be calculated using Equation 2 to have a critical angle $\theta_c$=30° under clean conditions (i.e., when in contact with air) and $\theta_c$=48.6° under contaminated conditions (i.e., in the presence of the residue). Therefore, light having an incident angle of, for example, $\theta_i$=52° should undergo TIR and produce evanescent waves under both conditions. The penetration distance of evanescent waves generated by light having an incident angle $\theta_i$=52° and a UV-C wavelength of 220 nm may be calculated using Equation 4 to extend about 28 nm from the surface when no residue is present at the waveguide surface, and to extend about 72 nm from the surface of the waveguide when a residue is present on the waveguide surface. Residues within this larger range of 0 to 72 nm (e.g., residues directly touching the surface) are affected by the light, but any objects positioned outside this range are not affected. As the angle of incident light approaches the critical angle, the penetration depth of the evanescent wave rapidly approaches a distance on the order of a single wavelength (e.g., 220 nm in this example), and when the incident light is equal to the critical angle, the penetration depth goes to infinity and light is refracted at the surface. Accordingly, the penetration depth of the evanescent wave can be configured by selecting a suitable combination of light wavelength, incident angle, and material refractive indexes. The evanescent waves may propagate along the transverse sides of the waveguide (e.g., parallel to the light propagating within the waveguide) for short distances.

Figure 5:
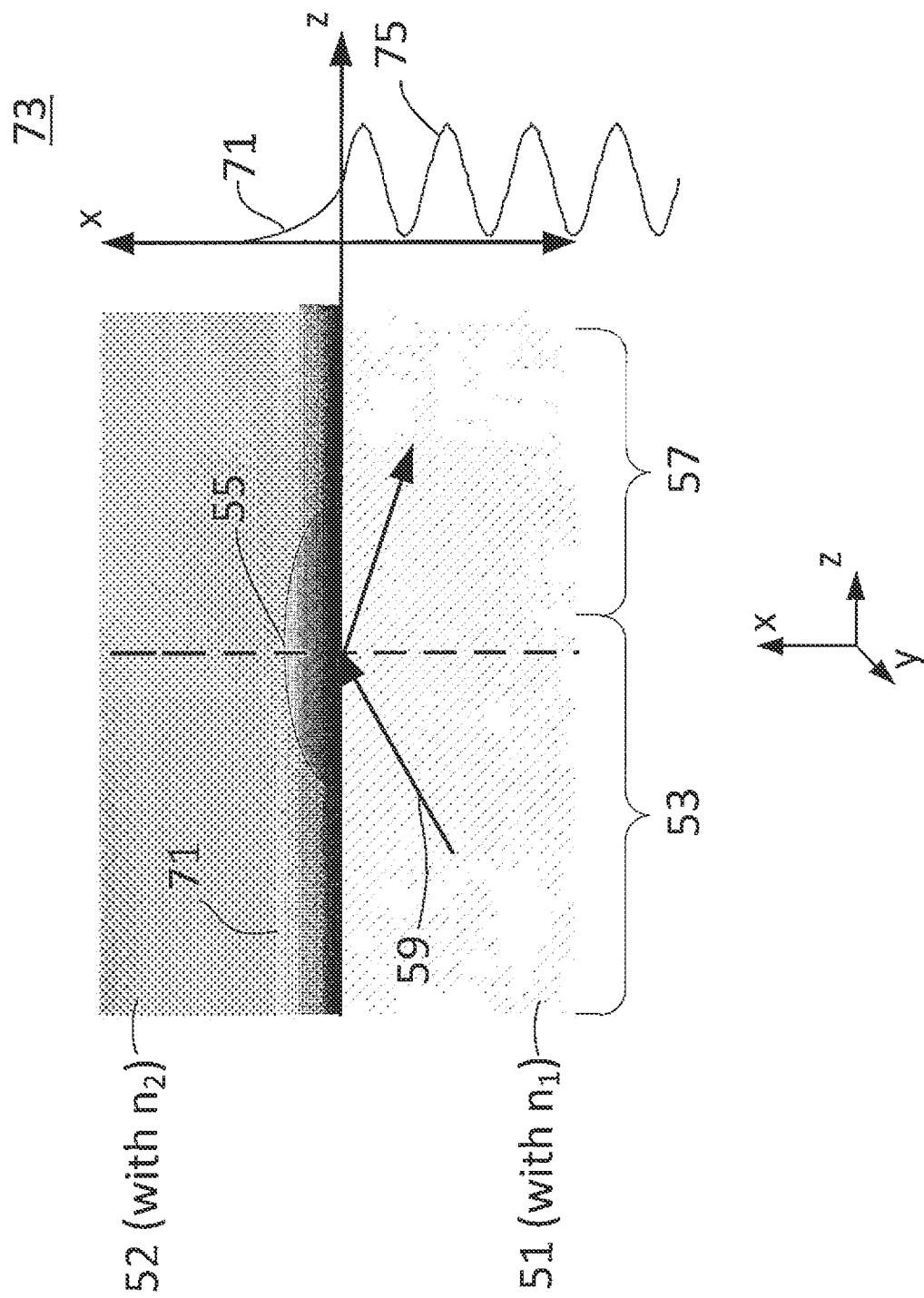
FIG. 5 is a schematic diagram illustrating an example embodiment in which a residue on the surface of a waveguide is exposed to light through the generation of an evanescent wave upon total internal reflection of light at the surface. The graph on the right side of the figure shows the exponential decay in the intensity/of the evanescent wave (z-axis) with respect to the distance d from the surface (x-axis) and the continuity of this wave with the sinusoidal wave corresponding to the totally internally reflected light within the waveguide.

FIG. 5 is a schematic diagram illustrating the generation of an evanescent wave 71 along the side of a waveguide 51 in contact with air 52 in a first region 53, and in contact with a residue 55 in a second region 57. The evanescent wave 71 is generated upon total internal reflection (TIR) of a ray of light 59 at the interface between the waveguide 51 and air 52 in the first region 53, and moves horizontally (e.g., along the z-direction) with respect to the surface of the waveguide 51. The graph 73 on the right side of the figure shows the exponential decay in the intensity I of the evanescent wave 71 (z-axis) with respect to the distance d from the surface (x-axis), along with the sinusoidal wave 75 corresponding to the x-vector component of the totally internally reflected light within the waveguide 51. The wave is observed to be continuous at the interface between the waveguide 51 and the air 52.

In some embodiments, the waveguide may further include a layer of metal on the side exposed to the user. In this case, evanescent waves may be alternatively generated through the excitation of surface plasmon polaritons (SPPs) at the air-metal interface upon excitation of the metal by light (e.g., a photon, such as a UV-C energy photon) having a suitable frequency and momentum. For example, arrays of aluminum nanoparticles have been observed to exhibit plasmon resonances as low as 215 nm (5.8 eV), as described in Maidecchi, et. al. ACS Nano, 7, 5834-5841 (2013), the entire content of which is incorporated herein by reference.

Figure 6:
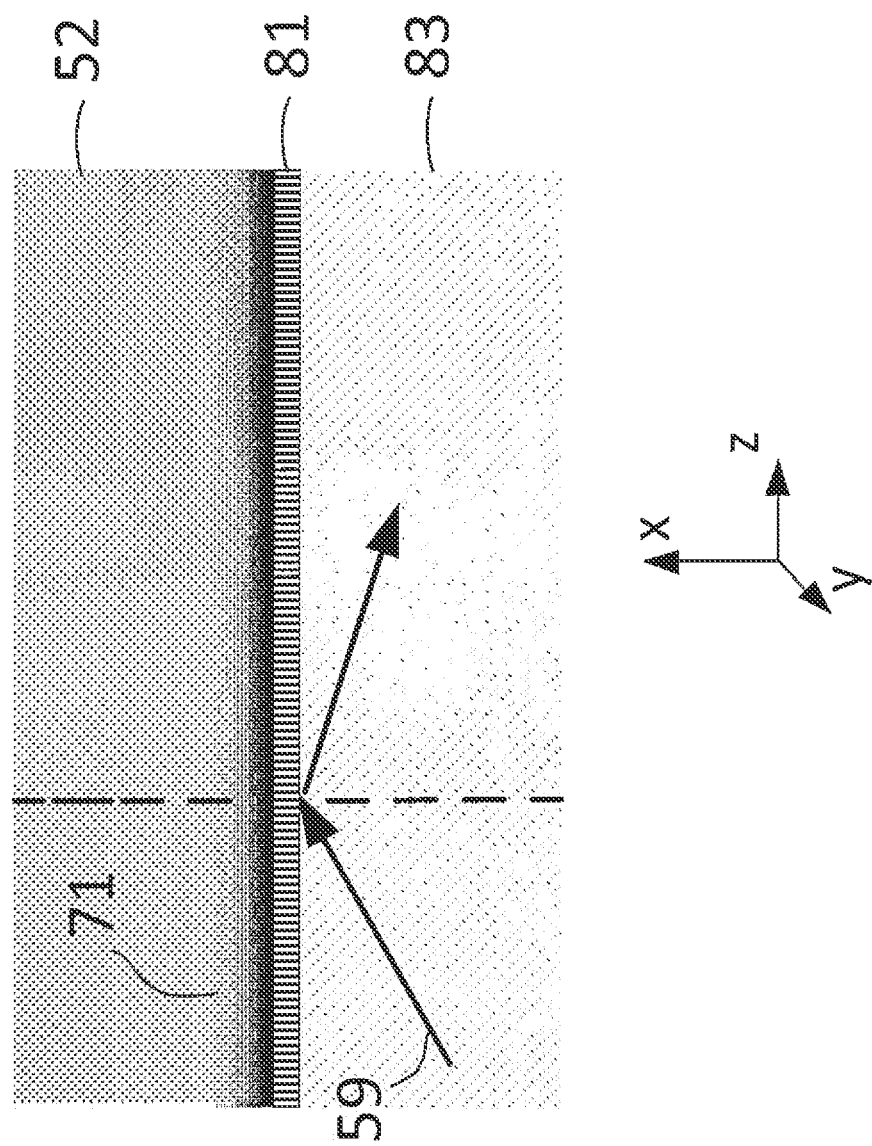
FIG. 6 is a schematic diagram illustrating the generation of a surface plasmonic position (SPP)-derived evanescent wave along an interface between a metal layer and air when incident light transmitted through an underlying translucent layer (e.g., the propagating material of a waveguide) is incident on the opposite side of the metal layer.

FIG. 6 is a schematic diagram illustrating the generation of an evanescent wave 71 along a metal layer 81 in air 52 when a photon (ray of incident light) 59 is transmitted through an underlying translucent layer 83 (e.g., the propagating material of a waveguide surface) and is incident on the opposite side of the metal layer 81. However, embodiments of the present disclosure are not limited thereto, and other configurations and combinations of parts suitable for producing SPP evanescent waves may be used. For example, various configurations for and methods of producing SPPs are described in Ye, F. et al, Nanophotonics, 3(1-2), 44-39 (2014), the entire content of which is incorporated herein by reference, and it will be understood that those having ordinary skill in the art are capable of integrating such configurations and methods with the surface structures described herein.

As a third exposure mechanism, residues on a waveguide surface may be exposed to light by scattering. In some embodiments, when a residue on the waveguide surface structure is larger (e.g., in scale or diameter) than the wavelength of the light propagated within the waveguide, any light transmitted at the surface (for example, light in the form of evanescent waves or refracted light due to a higher index of refraction) can be scattered to other residues on the surface via diffuse scattering. Such scattering occurs in all directions, and may release light at an intensity of about 0.25 to about 5 mW/cm$^2$, or about 0.25 to about 10 mW/cm$^2$. In some embodiments, the intensity ratio of scattered light in areas including such "large" residues compared to areas not including residues may be about 10 to about 100 times, or about 100 to about 1000 times as strong.

The mechanisms for refracting or transmitting UV light may operate sequentially or simultaneously. The self-sanitizing surface structures described in example embodiments of the present disclosure may be configured to emit light according to any one or any combination of the above described mechanisms. Furthermore, the specific mechanism or combination of mechanisms, the amount (flux) of light transmitted into the residue, and the specific conditions under which light is transmitted into the residue can be configured by selecting a suitable combination of incident angle, acceptance and/or injection angle, refractive index, and/or material geometry, in accordance with the principles described above.

Aspects of embodiments of the present disclosure provide a self-sanitizing surface structure. The self-sanitizing surface structure may include a waveguide, and the waveguide may include a propagating layer and a support layer. A first transverse side of the propagating layer (i.e., the side exposed to the user, or the upper side in the drawings) may be exposed to air and be configured to selectively refract light as described herein according to embodiments of the present disclosure, and a second transverse side of the propagating layer opposite the first transverse side may be in direct contact with the support layer. The propagating layer serves as a light propagating medium and may be alternatively referred to as the "core" of the waveguide. The support layer may be configured to reflect light as described herein according to embodiments of the present disclosure so that light within the propagating layer is not transmitted into or absorbed by any structures beneath it, and may also be referred to as cladding.

The material for forming the propagating layer should be transparent or mostly transparent to the wavelengths of light to be used within the self-sanitizing surface structure. As used herein, the term "transparent" may be used interchangeably with the term "optically transparent" to refer to a material capable of transmitting light without absorbing or scattering it. The term "mostly transparent" may refer to a structure than allows passage of at least about 85% of the incident light, for example at least about 90% of the incident light, or in some embodiments, about 99% of the incident light per cm travelled in the material. It will be understood that when a material is described as being "transparent", the material is transparent to at least the wavelength or wavelengths of interest, but may not be transparent to light of other wavelengths, and those having ordinary skill in the art are capable of determining which wavelengths are of interest according to the context and principles described herein.

The material for forming the propagating layer may be substantially amorphous (e.g., non-crystalline) to prevent or reduce scattering of light within the waveguide. The amorphousness of a material can be quantified using X-ray diffraction (XRD); amorphous materials do not exhibit any XRD peaks.

In some embodiments, the propagating layer may be formed of an inorganic material. Non-limiting examples of inorganic materials used to form the propagating layer may include UV grade amorphous silica (such as Corning® HPFS® 7979 or 7980 (Corning, Corning, New York), quartz glass, a metal sulfide (such as zinc sulfide (ZnS)), and metal fluorides (such as $MgF_2$, exhibiting >95-100% transmission at 220 nm). In some embodiments, the propagating layer may be formed of amorphous silica, which has the advantage of being cheaper than quartz.

In some embodiments, the propagating layer may be formed of an organic fluoropolymer. Non-limiting examples of fluoropolymers used to form the propagating layer may include a cyclic ether-containing fluoropolymer such as CYTOP® Type S (AGC Chemicals, Tokyo, Japan) (exhibiting 93-95% transmission at 220 nm), a PTFE-terpolymer such as Solaflon® (POM TV UG, Cologne, Germany) (exhibiting 85% transmission at 220 nm), polychlorotrifluoroethylene (PCTFE, also known commercially as Kel-F® (3M, Maplewood, MN), Clarus® (Honeywell, Morris Plains, NJ), and Neoflon® (Daikin, Osaka, Japan)) (exhibiting 90% transmission at 220 nm), a cyclic olefin copolymer (COC) such as TOPAS® 8007X10 (TOPAS Advanced Polymers, Frankfurt, Germany) (exhibiting 70% transmission at 280 nm), and polymethylpentene (PMP) (also known commercially as TPX™ (Mitsui Chemicals, Tokyo, Japan)) (grade RT18 exhibiting 70% transmission at 300 nm). In some embodiments, the waveguide surface may be formed of a cyclic ether-containing fluoropolymer such as CYTOP® and/or a PTFE-terpolymer such as Solaflon®.

In some embodiments, the propagating layer may be formed of a saturated hydrocarbon or aliphatic polymer. Non-limiting examples of hydrocarbon or aliphatic polymers used to form the propagating layer may include polystyrene (PS), polyvinyl chloride (PVC), and polymethyl methacrylate (PMMA).

The propagating layer is formed of a material having a refractive index larger than that of air (i.e., n>1.00). In some embodiments, the propagating layer may be formed of a material having a refractive index n of about 1.3 to about 2.5, for example, about 1.0 to about 2.0, about 1.2 to about 1.8, or about 1.3 to about 1.7.

The materials for forming the propagating layer may be treated in order to adjust or select a particular refractive index using any available method in the art. In some embodiments, for example, the materials may be subjected to mechanical stress and/or doped with impurities. In some embodiments, when the propagating layer is formed of a polymer, the polymer may be modified with additional moieties to adjust the refractive index. However, embodiments of the present disclosure are not limited thereto, and it will be understood that those having ordinary skill in the art are capable of selecting suitable materials, treatments, and treatment methods according to the desired properties of the propagating layer.

In some embodiments, the propagating layer forms the uppermost layer of the self-sanitizing surface structure, and as such, the propagating layer is largely in contact with air (n=1.00) on the side exposed to users. As such, when no residues are present on the surface of the waveguide and light is propagated within the waveguide, the light is incident against and reflected by the air-waveguide interface due to the higher refractive index of the propagating material (i.e., due to TIR, as described above). Further, when a residue is deposited on the top of the waveguide (i.e., the side exposed to users), the residue is deposited directly on the propagating layer. As such, the air-waveguide interface is replaced with a residue-waveguide interface at the point or area of deposition.

As described herein, when a residue-waveguide interface is formed on the surface of the waveguide, the critical angle for TIR within the waveguide at the point of contamination is changed (i.e., decreased), such that one or more wavelengths of light that were previously constrained within the waveguide may now be refracted at the residue-waveguide interface. The amount of light that may be refracted upon this change (e.g., the range of light having an angle of incidence larger than the critical angle at the air-waveguide interface, but smaller than the critical angle at the residue-waveguide interface) depends on the combination of residues, the ambient environment, and the materials for the propagating layer and other waveguide components. As such, the amount of light refracted at the surface of the waveguide may be controlled or selected by using a suitable injection angle (e.g., an injection angle that results in TIR in the absence of residue and refraction in the presence of residue, as described herein according to embodiments of the present disclosure) and a suitable combination of materials (e.g., a combination of refraction indexes that supports the TIR and refractive behavior as described above). In addition, the residue deposited on the waveguide may be further exposed to transmitted light via propagation of evanescent waves or by scattering, as described herein.

The propagating layer may have a layer thickness (e.g., between the air and the support layer) of about 0.1 mm to about 4 mm, for example, about 0.2 mm to about 3 mm, about 0.3 mm to about 2 mm, or about 0.4 mm to about 1 mm. The width and length of the propagating layer are not particularly limited.

The support layer is positioned directly adjacent to the second transverse side of the propagating layer, opposite the first transverse side exposed to the user. As described above, the support layer is selected so that light within the propagating layer is not transmitted into or absorbed by any structures beneath it. Further, the support layer is selected so that light within the propagating layer is reflected back into and remains within that layer when light is incident on the interface between the propagating layer and support layer.

In some embodiments, the support layer may include a layer that acts as an optical mirror. For example, the support layer may include a metal or metallic layer, coating, or structure that acts as a reflective mirror. Non-limiting examples of metals that may be included in the support layer may include, for example, silver (Ag), nickel (Ni), and/or aluminum (Al). When the support layer includes a metallic layer, the layer may be provided as a foil or a sheet that is attached by bonding to the second transverse side (i.e., lower side) of the propagating layer, or may be deposited on the propagating layer by, for example, spraying or evaporating.

In some embodiments, the support layer may include a layer that acts as a diffuse reflector, such as those made of porous polytetrafluoroethylene (PTFE) or porous silica (silicon). When the support layer includes a diffuse reflector layer, the layer may be provided as a sheet that is attached by bonding to the second transverse side (i.e., lower side) of the propagating layer.

In some embodiments, the support layer may include a transparent solid material having a refractive index lower than the refractive index of the propagating layer, such that a dielectric interface is formed. The transparent solid material may be any material having a suitable refractive index, as described herein, and for example, may be a low refractive index metal fluoride. Under the refractive index and critical angle conditions described herein with respect to Equation 2, light propagating within the propagating layer should exhibit total internal reflection at the boundary between the propagating layer and the support layer. As such, the support layer may be referred to as cladding on the second transverse side of the propagating layer.

In some embodiments, the support layer may include a layer of gas, such as air. For example, when the propagating layer is rigid enough to resist sagging and bending, the propagating layer may be suspended over a volume of air using one or more spacers. The spacers should be formed of a material that does not absorb light and is reflective or has a refractive index lower than the refractive index of the propagating layer.

The thickness of the support layer is not particularly limited as long as it is suitable for preventing or reducing light emission. In some embodiments, when the support layer forms a dielectric interface, the support layer may have a thickness of about 10 micron to about 1 cm, for example, about 100 micron to about 0.5 cm. In some embodiments, when the support layer is formed of a metal, the support layer may have a thickness of less than 1 mm, for example about 100 nm to about 100 micron, or 150 nm to 10 micron. The width and length of the support layer are not particularly limited as long as the support layer has the same or a larger footprint than the propagating layer.

In some embodiments, the self-sanitizing surface structure may further include a structural layer under the support layer. The structural layer may provide further structural support to the self-sanitizing surface structure, for example, to prevent or reduce sagging or bending when the propagating layer and support layer have thicknesses that are liable to such distortions. The thickness, width, and length of the structural layer are not particularly limited as long as they meet or supplement the requirements described herein for the support layer.

In some embodiments, the self-sanitizing surface structure may further include a UV light source. In some embodiments, for example, when the UV light source generates or spreads light in multiple directions (e.g., at multiple angles), the UV light source may be coupled to the propagating layer via optics (i.e., optical components) so that UV light generated by the UV light source can be injected into the propagating layer at a suitable angle (e.g., an injection angle that results in TIR in the absence of residue and refraction in the presence of residue, as described herein according to embodiments of the present disclosure).

Figure 7:
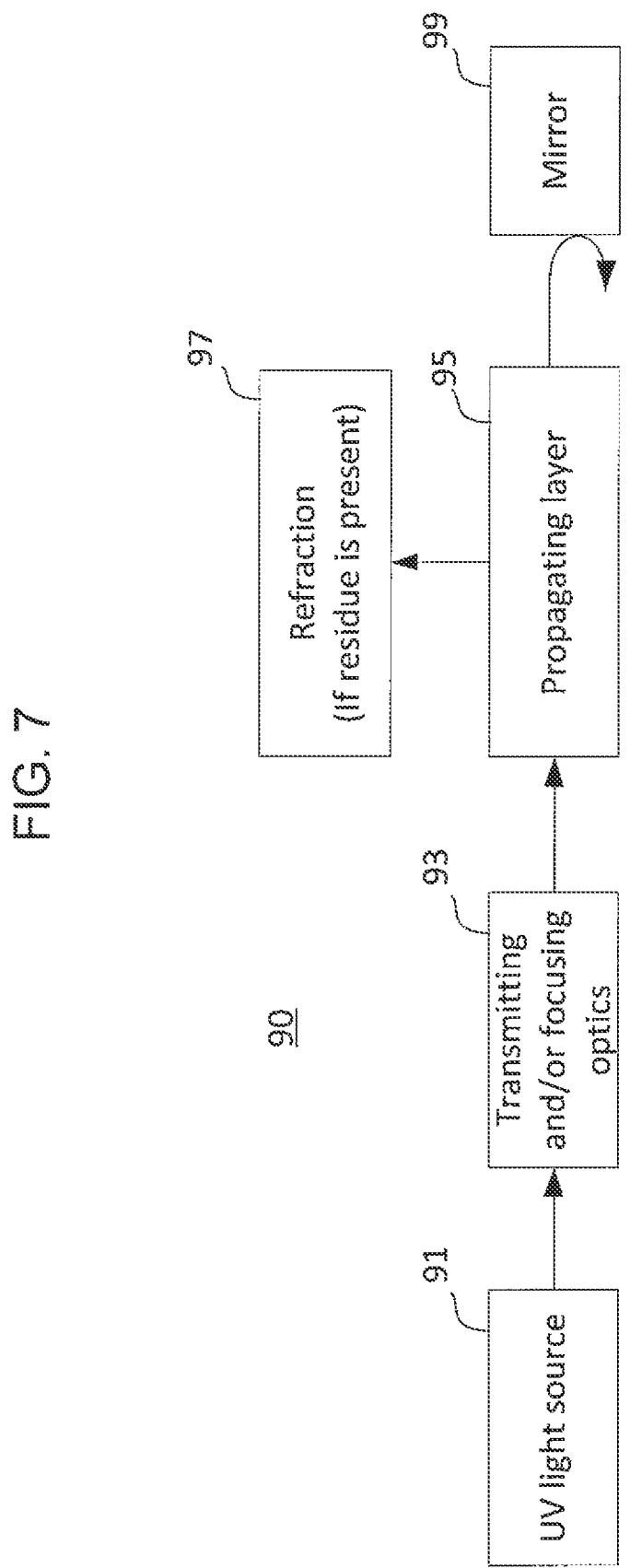
FIG. 7 is a block diagram describing the parts (including various optical components) and the movement of light through a self-sanitizing surface structure according to embodiments of the present disclosure.

FIG. 7 is a block diagram 90 describing the parts (including various optical components) and the movement of light through a self-sanitizing surface structure according to embodiments of the present disclosure. A UV light source 91 provides light to transmitting and/or focusing optics 93 so that the light is injected into a waveguide propagating layer 95. If a residue is present on the waveguide propagating layer 95, refraction 97 of a portion of the light occurs at the location of the residue. The remaining portion of the light remains in the waveguide propagating layer 95, and may be reflected by a mirror 99 positioned at the terminal end of the waveguide propagating layer 95, so that the light remains within the waveguide propagating layer 95 instead of exiting the layer.

The UV light source may be selected to produce light having one or more wavelengths of interest at a suitable intensity for surface decontamination. In some embodiments, the UV light source may produce multiple wavelengths and/or a wide range of wavelengths, but be filtered to restrict the range of emitted wavelengths to a narrower sub-range or specific wavelengths.

In some embodiments, the UV light source may be selected to produce UV-A, UV-B, and/or UV-C light. In some embodiments, for example in biodecontamination applications, the UV light source may preferably produce UV-C light (e.g., light having wavelengths of about 200 nm to about 280 nm or about 200 nm to about 290 nm), but embodiments of the present disclosure are not limited thereto. UV-C light is known to have germicidal effects and is not able to penetrate past the upper dead layer of human skin despite its higher energy, due to increased absorption and scattering of light in this wavelength range by biomolecules located in this layer of skin. The use of UV-C light for germicidal purposes as applied using a KrBr excimer lamp and transmitted through air is described in, for example, Buonanno et al., "207-nm UV Light—A Promising Tool for Safe Low-Cost Reduction of Surgical Site Infections. I: In Vitro Studies", *PLOS One*, October 2013, 8(10), e76968, the entire content of which is incorporated herein by reference.

The UV light refracted at the surface of the self-sanitizing surface structure may be selected to target one of more types or kinds of biological residues. For example, UV light having a wavelength of less than or equal to about 250 nm has an energy suitable for breaking the chemical bonds of amino acids, thus denaturing essential proteins. UV light having a wavelength of greater than or equal to about 250 nm has an energy suitable for breaking nucleic acids such as DNA and RNA, which can trigger apoptosis, necrosis and/or lysis in cells, or inactivate a virus. The terms "apoptosis" and "necrosis" are used in their art-recognized sense to refer to any suitable mechanism of programmed or sudden premature cell death, including mechanisms that result in genetic material degradation and membrane disruption. The terms "lysis" and "lyse" are used in their art-recognized sense to refer to disruption or breakage of a cell's membrane with concomitant release of its contents, thereby resulting in cell death.

In some embodiments, the UV light refracted at the surface of the self-sanitizing surface structure may be selected to target chemical residues. Many organic bonds included in residues such as toxins, chemical weapons, and explosive residues have bond dissociation energies that match the energy available from UV light. For example, many toxins, chemical weapons, and explosive compounds include one or more carbon-nitrogen (C—N), carbon-phosphorus (C—P), and/or carbon-carbon (C—C) bonds. When UV light having an energy equal to or greater than the dissociation energy of a bond is applied to the molecule, the bond may be broken and the activity of the organic compound may be destroyed. FIG. 8 includes a list of various chemical bonds, their dissociation energies, and the corresponding wavelength of UV light required to initiate bond dissociation. The data in FIG. 8 is reproduced from Table 2.10 in Tsia, K. ed., *Understanding Biophotonics: Fundamentals, Advances, and Applications,* 2015, Taylor and Francis Group LLC, Boca Raton, FL, the entire content of which is incorporated herein by reference. Additional bond types and energies can be found in other references in the art, such as Dean, J. A., *Lange's Handbook of Chemistry,* 15th ed., 1998, McGraw-Hill, New York, NY, the entire content of which is incorporated herein by reference.

References listing chemical bond dissociation energies in kJ/mol can be converted to the corresponding UV light wavelength according to Equation 5:

$$\lambda = h*c/E = h*c/\{[\text{dissociation energy (in kJ/mol)}]/N_A\} \quad \text{Equation 5}$$

where c is the speed of light ($2.998*10^8$ m s$^{-1}$), h is Planck's constant ($6.6260755*10^{-34}$ J s), and $N_A$ is Avogadro's constant ($6.022*10^{-23}$ units mol$^{-1}$). For example, a bond dissociation energy of 598 kJ/mol corresponds to 200 nm UV light, and a bond dissociation energy of 342 kJ/mol corresponds to 350 nm UV light.

FIG. 9 is a chart providing additional examples of the energies for phosphorus- and nitrogen-containing bonds in kJ/mol, reproduced from Table 4.11 ("Bond Dissociation Energies") from Dean, J. A., *Lange's Handbook of Chemistry*, 15th ed., 1998, McGraw-Hill, New York, NY.

The example materials described herein for forming the propagating layer are typically more transparent as the wavelength of light is increased. In some embodiments, this may be due to a lesser degree of absorption by chemical bonds within the material. Accordingly, the wavelength of light may be changed or selected in order to achieve better optical properties with respect to a particular waveguide material, although the suitability of the wavelength for decontamination should also be a factor for consideration.

In some embodiments, the UV light source may include a single lamp. In some embodiments, the UV light source may include multiple lamps. Non-limiting examples of suitable UV light sources may include excimer lamps (such as KrCl, which emits at 222 nm), downshifting excimer lamps (such as Xe$_2$, which emits at 172 nm and is downshifted with a phosphor to 220 nm to 290 nm), an excimer laser, a LED, a mercury (Hg) vapor lamp (which emits at 254 nm), and light sources including AlGaN quantum wells. In some embodiments, the UV light source may be a Hg vapor lamp or an excimer tube lamp.

Non-limiting examples of optics (optical components) for coupling the UV light source to the propagating layer may include collimating optics, mirrors, refractive lenses, reflective lenses, and optical fibers. When the optics include lenses, non-limiting examples of such lenses may include metamaterial-based lenses, Fresnel lenses, etc. Further, the lenses may be narrow-band lenses as long as they are suitably compatible with the wavelengths generated by the UV light source. When the optics include optical fibers, the fibers may be standard single mode fibers, multimode fibers, hollow core or solid core photonic crystal fibers, etc. The optical fibers should be at least partially transmissive to UV light, for example, at least about 50% transmissive, at least about 65% transmissive, or at least about 80% transmissive.

FIGS. 10A-10H are schematic diagrams showing various example embodiments of optical components that may be connected to the propagating layer 105 of a self-sanitizing surface structure having an upper transverse surface 111 containing a residue 109, a lower transverse surface 112, a first longitudinal side 113, and a second longitudinal side (terminal end) 114.

FIG. 10A shows an example embodiment of a self-sanitizing surface structure 100 in which the optics include a UV light source (e.g., a lamp or bulb) 101, a mirror box 107 surrounding the UV light source 101, and a focusing lens 103. The UV light source 101 is coupled to the first longitudinal side 113 of the propagating layer 105 via the focusing lens 103 in order to inject the light 115 produced by the UV light source 101 into the propagating layer 105 at a particular angle or set of angles (as described in detail according to embodiments of the present disclosure herein). The mirror box 107 traps light produced by the UV light source 101 that may be directed away the self-sanitizing surface structure 100 and reflects said light toward the focusing lens 103 in order to increase the efficiency or flux of light 115 that is injected into the propagating layer 105.

FIG. 10B shows an example embodiment of a self-sanitizing surface structure 120 in which the optics include a UV light source 101, a mirror box 107 surrounding the UV light source 101, and a focusing lens 103 as in FIG. 10A, as well as a mirror 117 on the terminal end 114 of the propagating layer 105. The mirror 117 reflects light 115 that would normally refract and exit the propagating layer 105 at its terminal end 114, thereby preventing or reducing loss of flux from the propagating layer 105 at that end. In addition, the UV light source 101 and focusing lens 103 are positioned at an angle less than 180° from the plane of the self-sanitizing surface structure 120 to thereby modify the injection angle of the light 115. It will be understood that the particular position of the UV lamp with respect to the self-sanitizing surface structure 120 is merely illustrative, and other positional angles or distances may be selected according to the principles described herein.

FIG. 10C shows an example embodiment of a self-sanitizing surface structure 130 in which the optics include a UV light source 101, a mirror box 107 surrounding the UV light source 101, a first focusing lens 103, and a second focusing lens 131. The UV light source 101 is coupled to the first longitudinal side 113 of the propagating layer 105 via the focusing lenses 103 and 131 in order to inject the light 115 produced by the UV light source 101 into the propagating layer 105 at a particular angle or set of angles (as described in detail according to embodiments of the present disclosure herein). It will be understood that the particular combination of biconvex lenses 103 and 131 shown in FIG. 10C is merely illustrative, and that other combinations, numbers, and types or kinds of lenses that may be suitably used to focus and/or direct light into self-sanitizing surface structures according to the embodiments herein. The number of lenses is not particularly limited, and may be 1, 2, 3, 4, etc. Non-limiting examples of suitable kinds of lenses include biconvex, piano-convex, positive meniscus, negative meniscus, piano-concave, and biconcave lenses, and may be used in any suitable combination (e.g., a combination that results in injection of light at an angle that enables selective refraction in the presence of a residue, as described herein according to embodiments of the present disclosure).

In some embodiments, one or more optical components may be positioned so that light is injected into the propagating layer at a longitudinal side of the layer, for example, on a third side perpendicular to the first and second transverse sides (e.g., side 113 of the propagating layer 105, as shown in FIGS. 10A-C). For example, when the self-sanitizing surface structure includes a channel structure waveguide that extends in the z direction and is guided (limited) along the x and y directions, the optics may be coupled to a plane having a normal substantially parallel to ±z. The side of the propagating layer coupled to the UV light source via the optics may be alternately referred to herein as the beginning side, injection end, or injection side (referring to injection of light), and the opposite or remaining sides may be referred to as the terminating side(s), terminating end(s) (referring to the end point of the propagated light), or non-injection side(s)) (e.g., side 114 as shown in FIGS. 10A-C).

In some embodiments, one or more optical components may be positioned so that light is injected into the propagating layer at a transverse side of the propagating layer (e.g., side 111 or 112 of the propagating layer 105, as shown in FIGS. 10A-C). For example, when the self-sanitizing surface structure includes a channel structure waveguide that is guided along the x and y directions and extends in the z direction, the optics may be coupled to a plane having a normal perpendicular to ±z. In some embodiments, for example when the optics include a prism or a grating, the optics may be positioned on the upper surface of the propagating layer.

FIG. 10D shows an example embodiment of a self-sanitizing surface structure 140 in which the optics include a UV light source 101, a mirror box 107 surrounding the UV light source 101, a first focusing lens 103, a terminal end mirror 117, and a prism 141. The UV light source 101 is coupled to the propagating layer 105 via the focusing lens 103 and the prism 141 in order to inject the light 115 produced by the UV light source 101 into the propagating layer 105 at a particular angle or set of angles (as described in detail according to embodiments of the present disclosure herein).

FIG. 10E shows an example embodiment of a self-sanitizing surface structure 150 in which the optics include a UV light source 101, a mirror box 107 surrounding the UV light source 101, a first focusing lens 103, and a diffraction grating 151. The UV light source 101 is coupled to the propagating layer 105 via the focusing lens 103 and the diffraction grating 151 in order to inject the light 115 produced by the UV light source 101 into the propagating layer 105 at a particular angle or set of angles (as described in detail according to embodiments of the present disclosure herein).

In some embodiments, when the UV light source is a LED, the LED may include an integrated lens (e.g., a lens may be included or embedded in the LED housing, for example, between the luminescent emission layer and the irradiation target). In some embodiments, the LED with an integrated lens may be coupled to the propagating layer without the use of any additional and/or intermediate lenses. In some embodiments, the LED with an integrated lens may be coupled to the propagating layer by further utilizing one or more additional optical components as described above.

FIG. 10F shows an example embodiment of a self-sanitizing surface structure 160 in which the optics include an LED laser 161 with an integrated lens 163. The laser light is focused and injected into the side 113 of the propagating layer 105 at a particular angle or set of angles (as described in detail according to embodiments of the present disclosure herein). FIGS. 10G and 10H show an example embodiment of a self-sanitizing surface structure 170 in which the optics include a led laser 171 without an integrated lens. The laser light is directly injected into the side 113 of the propagating layer 105 at any suitable angle smaller than the acceptance angle 173, and may be rotated away from 180°, as shown in FIG. 10G, to select an injection angle that may enable selective refraction, as shown in FIG. 10H and as described herein according to embodiments of the present disclosure.

In some embodiments, the propagating material may be coupled to the UV light source via a prism or a grating positioned in contact with the surface, where the prism or grating is configured to inject light into the propagating material. The size, shape, and material of the prism is not particularly limited. In some embodiments, when the propagating material is coupled to a grating, the grating may be etched into an exposed portion of the waveguide (e.g., a portion that is not covered by cladding). In some embodiments, the grating may be deposited as a thin film or layer on top of an exposed portion of the waveguide.

The UV light should be introduced (injected) into the self-sanitizing surface structure at a suitable injection angle so that the resulting angle of incident light at the boundaries of the propagating layer is larger than the critical angle for a clean surface structure (e.g., in contact with air), but smaller than the critical angle for a contaminated surface structure (e.g., in contact with a residue, such as a microorganism containing water). When this condition is fulfilled, UV light is constrained within the surface structure under normal (clean) conditions, but is refracted at the sides of the surface structure under contaminated (residue) conditions until the residue is killed, removed, or degraded upon photoreaction with the light. As such, the amount of light the waveguide may be controlled or selected by using a suitable injection angle or range of injection angles, as determined by the combination of materials and refraction indexes as described herein according to embodiments of the present disclosure.

In some embodiments, for example, the UV light is injected into the self-sanitizing surface structure within the acceptance angle of the propagating layer. In some embodiments, the UV light is injected into the sanitizing surface structure at an angle that is within the acceptance angle of the propagating layer under clean conditions, but outside of the acceptance angle of the propagating layer under contaminated conditions.

In some embodiments, substantially all of the UV light is injected into the self-sanitizing surface structure within the acceptance angle. In other embodiments, a fraction of the UV light is injected into the self-sanitizing surface structure within the acceptance angle. In some embodiments, for example, about 10%, about 20%, about 30%, about 40%, about 50%, about 60%, about 70%, about 80%, or about 90%, of the UV light is injected into the self-sanitizing surface structure within the acceptance angle. In some embodiments, about 20% to about 80%, about 30% to about 70%, or about 40% to about 60% of the UV light is injected into the self-sanitizing surface structure within the acceptance angle.

In some embodiments, when UV light is used within the self-sanitizing surface structure, decontamination, specifically decontamination of biological agents, may be achieved without the use of germicidal coatings or layers.

In some embodiments, the self-sanitizing surface structure may further include a thin metal coating on the first transverse side of the propagating layer (i.e., the side exposed to the user). In this case, residues are deposited on the metal coating, and photons transmitted from the propagating layer to the metal coating generate surface plasmon polaritons (SPPs), as described above. The thin metal coating may have any suitable thickness, for example, about 10 nm to about 500 nm. In some embodiments, the metal coating may be deposited on the entire first transverse side of the propagating layer, or may be deposited on only a portion of the first transverse side of the propagating layer.

In some embodiments, the self-sanitizing surface structure may further include an optical mirror at a terminating longitudinal side of the propagating layer. The optical mirror may be used to reflect light back into the waveguide and to prevent or reduce light from being refracted at that boundary. The mirror may be planar or non-planar. In some embodiments, the optical mirror may be a thin sheet of film of a metal, such as aluminum, silver, or nickel. In some embodiments, the optical mirror may be a diffuse reflector, such as those made of porous polytetrafluoroethylene (PTFE). In some embodiments, when the waveguide is a slab or planar waveguide structure having four longitudinal sides, one of which is the injection end coupled to the UV light source via optics, an optical mirror may be positioned at one, two, or three of the remaining sides (e.g., terminating and/or longitudinal sides).

In some embodiments, the self-sanitizing surface structure may further include a mirror box (e.g., an enclosure having mirrored inside walls) around the UV light source, for example, to direct light produced by the UV light source into the propagating layer, or to prevent or reduce unwanted radiation loss from the UV light source. The dimensions, materials, etc. used to form the mirror box are not particularly limited and may be suitably selected by those having ordinary skill in the art according to the principles described herein.

In some embodiments, the self-sanitizing surface structure may be formed over a substrate. For example, the substrate may be under the support layer. The substrate may have any arbitrary shape or topology, such as that of a doorknob, counter surface, railing, etc. In some embodiments, the substrate may be at least part of a room fixture or furniture item such as a table, counter, wall, floor, roof, ceiling, chair, toilet, etc., or may be part of a device or object such as a handle, grip, case, etc. In some embodiments, the self-sanitizing surface structure may be formed over the surface of a substrate formed of conventional materials (e.g., as a cover or top surface). In some embodiments, when the substrate is reflective or has a lower refractive index than the propagating layer, the substrate may also function as a support layer, and can be used directly under the propagating layer of the self-sanitizing surface structure (e.g., without a support layer).

The self-sanitizing surface structure and its constituent parts may have any suitable footprint and curvature, i.e., any curvature that allows the waveguide to prevent or constrain the refraction of light along the surfaces of the waveguide when the waveguide is in contact with air, and to refract light when the waveguide is in contact with a residue having a refractive index larger than that of air, for at least one set (range) of incident angles. The curvature may be uniform or non-uniform across the footprint of the surface structure, and may be symmetric or non-symmetric. In some embodiments, the self-sanitizing surface structure and its constituent parts may each have substantially no curvature, such that they are substantially planar (flat). In some embodiments, the self-sanitizing surface structure and its constituent parts may each be non-planar so as to conform to a curved or non-planar underlying surface. It will be understood that when at least one portion of the self-sanitizing surface structure has non-zero curvature, the geometry of the interaction of light transmitted within the waveguide with the surfaces of the waveguide (i.e., the angle of incidence) may vary across the waveguide surface, such that it may become more difficult to select a suitable combination of injection angle and material. However, those having ordinary skill in the art are capable of selecting such configurations according to the principles described herein.

The self-sanitizing surface structure may be configured to refract a suitable amount of UV light in response to a particular type of residue or application. For example, the surface may be configured to refract about 0.01% to about 25%, and in some embodiments, about 0.1% to about 20%, about 1% to 10%, or about 2% to 5% of a UV light transmitted within the propagating layer (i.e., with respect to the total flux of the UV light) when a residue is positioned on the first transverse side. Furthermore, the amount of UV light transmitted at the surface of the self-sanitizing surface structure may be tuned by selecting suitable parameters in order to favor one or more exposure mechanisms, as described herein, for example, by changing the insertion angle of the UV light.

As described above, the self-sanitizing surface structure may be configured to selectively refract light only when a residue is present, and at an interface with the residue. That is, light is not refracted indiscriminately along the entire surface of the self-sanitizing surface structure, and is refracted only in specific portions or regions of the self-sanitizing surface structure, under specific conditions. From another perspective, the self-sanitizing surface structure may refract light along less than 100% of the surface of the self-sanitizing surface structure, for example, less than about 70%, less than about 50%, less than about 40%, less than about 30%, less than about 20%, etc.

In some embodiments, the propagation of light within the waveguide may be limited to one or more modes. The term "mode" is used herein in its art-recognized sense to refer to a standing wave that is able to exist within and propagate through the waveguide, and is "allowed" given the boundary conditions (geometry) of the waveguide. A mode also denotes a solution of the wavefunction describing the propagation of an electromagnetic wave through a waveguide. A light wave that is injected to the waveguide at an angle or frequency that does not match one of the allowed modes of the waveguide is unable to propagate through the waveguide.

A light wave injected into a planar waveguide at a non-zero injection angle bounces back and forth between opposing sides of the waveguide as it traverses the distance of the waveguide. The propagation of the light wave thus includes multiple segments, the trajectory of each of which can be separated into a transverse component (for example, a vector in the x direction) and a longitudinal component (for example, a vector in the z direction). FIG. 11 is a schematic diagram illustrating the first four (lowest energy) modes (i.e., wavefunction solutions) of the transverse component of a light wave 205 undergoing TIR and propagation within a waveguide 200 that is limited along a dimension (x) to have a width d and is composed of a central propagating material 201 surrounded by cladding 203 (e.g., air) along the sides perpendicular to the x-axis. The light waves associated with each mode are alternatingly of cosine and sine form, where m is the index of the mode, 0 denoting the fundamental mode having 0 nodes (i.e., points of waveform cross-over with the z-axis, where a larger number of nodes is correlated with higher wave frequencies and energies). The energies associated with the light wave increase from left to right as the index of the mode increases. The "bleeding" of the sine and cosine waveforms beyond the interface between the central propagating material 201 and the cladding 203 is explained in more detail herein, in connection with the discussion of evanescent waves.

From another perspective, the transverse component segments of the light wave's trajectory through the waveguide are superimposed and thus subject to constructive or destructive interference. When the transverse component segments of the light wave interfere constructively (resonate), all points of the wavefront are in phase, and light is able to propagate through the waveguide. The superimposition of the transverse component segments results in a waveform such as those depicted in FIG. 4. However, when the transverse component segments of the light wave interfere destructively, light does not propagate.

The geometry of the waveguide, the angle of incidence, and the frequency (wavelength) of light affect the relative phase of each transverse component segment and thus determine whether interference along the transverse component occurs constructively or destructively, and thus whether light can propagate through the waveguide. Specifically, for constructive interference to occur, the phase of each transverse component segment can only vary by ±2πm, where m is any integer.

The number of allowed modes, and/or the geometric conditions under which constructive interference occurs and light propagates through a symmetric waveguide along a given coordinate may be expressed in terms of Equations 6 and 7:

$$V = (dk_0/2)(n_1^2 - n_2^2)^{1/2} \quad \text{Equation 6}$$

$$V_m = m\pi/2 \quad \text{Equation 7}$$

where V is a dimensionless parameter used to describe the number of modes in the waveguide, d is the distance between the sides of the waveguide along the coordinate of propagation (e.g., $d_x$ or $d_y$ in the channel waveguide of FIG. 1A, or $d_x$ in the slab waveguide of FIG. 1B), $k_0$ is the wavenumber of the light wave (e.g., $2\pi/\lambda$), $n_1$ is the refractive index of the propagating material, $n_2$ is the refractive index of any cladding and/or the surrounding material (e.g., air) along the transverse surfaces of the waveguide (as shown in, e.g., FIG. 3 and FIG. 11), $V_m$ refers to a mode of the waveguide having an index m, and m is any integer greater than or equal to 1. The parameters $n_1$, $n_2$, and d are determined by the materials and dimensions used to construct the waveguide, while $k_0$ is a property of the light injected into the waveguide. These parameters collectively determine the dimensionless parameter V, which sets the upper limit of $V_m$ in Equation 7. A mode $V_m$ is allowed when the quantity mπ/2 is less than V. When $V_m$ is larger than V, the mode is not allowed in the waveguide, and light cannot propagate within the waveguide at that mode. For example, when the quantity $V=(dk_0/2)(n_1^2-n_2^2)^{1/2}$ is about π/2, only m=0 (the fundamental mode having 0 nodes) is allowed. When a waveguide has V=10, $V_6=3\pi \approx 9.42$, while $V_7>10$, and thus the waveguide allows 7 modes ($V_0$ to $V_6$), with modes corresponding to $V_7$ and above not allowed. From these examples, it can be seen that a larger number of modes can be supported by increasing the values of d, $k_0$, and the difference between $n_1$ and $n_2$.

From another perspective, as the index of a mode increases, the frequency with which the light wave bounces off the sides of the waveguide increases, and the angle at which light bounces off the sides of the waveguide decreases with respect to the normal. As discussed above, when the angle of incidence is decreased to an angle smaller than the critical angle, light no longer undergoes TIR and is transmitted outside of the waveguide. As such, at a large enough mode, the angle of incidence becomes smaller than the critical angle and light is lost to transmission.

It will be understood that although Equations 6 and 7 herein refer to propagation within a symmetric two-dimensional (slab structure) waveguide, those having ordinary skill in the art are capable of generalizing or deriving the equivalent equations for additional cases, including channel structure waveguides and waveguides in an asymmetric environment (e.g., having different materials as cladding on each side).

In some embodiments, the waveguide may be configured to support single mode waveguiding behavior. The waveguide may have a channel structure or a slab structure. For example, $n_1$, $n_2$, and d of the waveguide and $k_0$ of the injected light may be selected so that only the fundamental mode is able to propagate within the waveguide. When a waveguide is a single-mode waveguide, the thickness of the waveguide may be constrained to the order of one or two wavelengths. Examples of waveguide materials, parameters, and light sources fulfilling these parameters are described herein, and it will be understood that those having ordinary skill in the art are capable of selecting suitable combinations of such materials and light sources according to the examples and principles described herein.

In some embodiments, the waveguide may be configured to support multimode waveguiding behavior. The waveguide may have a channel structure or a slab structure. For example, $n_1$, $n_2$, and d of the waveguide and $k_0$ of the injected light may be selected so that two or more modes are able to propagate within the waveguide. Examples of waveguide materials, parameters, and light sources fulfilling these parameters are described herein, and it will be understood that those of skill in the art are capable of selecting suitable combinations of such materials and light sources according to the examples and principles described herein.

In some embodiments, the self-sanitizing surface structure may include a single waveguide having a slab structure. For example, the slab structure waveguide may have a broad surface area sufficient to cover the surface of interest.

In some embodiments, the self-sanitizing surface structure may include a first waveguide and at least one additional waveguide adjacent to the first waveguide (e.g., two or more parallel and adjacent waveguides, or an array of waveguides); and parallel feeding optics or optics splitters to divide input UV light into the end of the propagating layer of each waveguide. In some embodiments, the self-sanitizing surface structure may include an array of single-mode waveguides, for example, an array of single-mode channel waveguides. Such an array may have the advantage of allowing greater control over the propagation and distribution of light in order to avoid local variations in the intensity of refracted light (e.g., hotspots and weak spots). When the self-sanitizing surface structure includes multiple parallel channel waveguides, the materials for each waveguide may be selected independently.

Aspects of embodiments of the present disclosure provide a method of fabricating a self-sanitizing surface structure. The self-sanitizing surface structure may be configured to selectively refract light (e.g., only in the presence of a contaminating residue, as described herein). The method includes: attaching a waveguide to a substrate, the waveguide including a propagating layer; and coupling a UV light source to an injection end of the propagating layer.

In some embodiments, the waveguide may further include a support layer between the propagating layer and the substrate. As such, the method of fabricating a self-sanitizing surface structure may further include attaching the support layer to a substrate. For example, the attaching the support layer to a substrate may be carried out prior to attaching the waveguide to the support layer, but embodiments of the present disclosure are not limited thereto.

In some embodiments, one or more components of the waveguide, including the propagating layer and the support layer, may be separately formed and subsequently attached to the substrate. For example, materials for forming the propagating layer and/or the support layer may be obtained as layers, films, or foils that are cut or shaped into a suitable size for the substrate. The materials may be attached to the substrate using any suitable method, as long as the bonding method does not interfere with propagation of light within the waveguide, for example, by absorbing light or introducing a non-reflective interface on the waveguide surface. For example, the propagating layer and the support layer may be attached to the substrate using an adhesive.

In some embodiments, one or more components of the waveguide, including the propagating layer and the support layer, may be formed in situ and directly on the substrate. For example, the attaching the waveguide to a substrate may include depositing a suitable material for the support layer and/or the propagating layer on the substrate. When the waveguide includes a propagating layer without a support layer, the propagating layer may be deposited directly on the substrate. When the waveguide includes a support layer and a propagating layer, the support layer may be deposited directly on the substrate, and the propagating layer may be deposited directly on the support layer.

The method or techniques used to deposit the material for the support layer and/or the propagating layer are not particularly limited, and may be selected according to the desired material and structure (e.g., thickness) of each. In some embodiments, when the material for the support layer is a metal layer, the metal may be deposited by spraying, sputtering, spin coating, etc. In some embodiments, when the material for the support layer is a polymer having a lower refractive index than the propagating material, the polymer may be deposited by applying a pre-polymer solution (e.g., a solution containing monomers and oligomers) to the substrate, and curing the coating. The depositing the pre-polymer solution may be accomplished via any suitable method, including spraying, spin-coating, dip coating, evaporation, etc. The curing may be accomplished using any suitable method, including heating and UV-irradiation, depending on the type of polymer.

In some embodiments, when the material for the support is a layer of air, supportive structures for suspending the propagating layer above the layer of air may be formed of any suitably supportive and non-absorbing material such as metal, optically reflective PTFE, etc., and may be attached to the substrate and the propagating layer using the same methods described in connection with the separately formed layers.

In some embodiments, when the material for the propagating layer is a UV-transparent polymer or fluoropolymer, the polymer may be deposited by applying a UV-transparent pre-polymer solution (e.g., a solution containing monomers and oligomers) to the substrate, and curing the coating. The depositing the UV-transparent pre-polymer solution may be accomplished via any suitable method, including spraying, spin-coating, dip coating, evaporation, etc. The curing may be accomplished using any suitable method, including heating and UV-irradiation, depending on the type of polymer. The UV-transparent polymer or fluoropolymer produced by the UV-transparent polymer may be the same as described herein in connection with the self-sanitizing surface structure.

In some embodiments, the area for depositing the propagating layer may be selected by using optical mirrors to define the sides of the propagating layer, as well as to prevent or reduce light transmission at the edges of the self-sanitizing surface structure. In some embodiments, the method may further include attaching optical mirrors to longitudinal sides of the substrate, the optical mirrors having a height larger than that of the substrate; and depositing the suitable material for the propagating layer on the substrate between the optical mirrors. In other embodiments, the method may include attaching the optical mirrors to the upper surface of the substrate at positions that define the outer area (e.g., one or more longitudinal sides) of the propagating layer. In other embodiments, the area for depositing the propagating layer may be selected using, for example, a deposition mask, and optical mirrors may be subsequently attached to the sides of the propagating layer using any suitable technique, as described above.

In some embodiments, the method of fabricating a self-sanitizing surface structure may further include depositing a metal layer on the propagating layer, the metal layer being configured to generate surface plasmon polaritons (SPPs). The metal layer may be the same as described herein in connection with the self-sanitizing surface structure.

The properties and materials of the substrate, optical mirrors, propagating layer, support layer, UV light source, and metal layer may each be the same as described herein with respect to the self-sanitizing surface structure, but embodiments of the present disclosure are not limited thereto.

In some embodiments, the self-sanitizing surface structure may be fabricated as an array of two or more adjacent and/or parallel surfaces. Each of the adjacent and/or parallel surfaces may be deposited using similar materials, methods, and parameters as described above for the single surface. The array of surfaces may be deposited simultaneously or successively.

In some embodiments, the method of fabricating a self-sanitizing surface structure may include attaching optical mirrors to longitudinal sides of a substrate, the optical mirrors having a height larger than that of the substrate; forming the support layer on the substrate between the optical mirrors; forming the propagating layer by applying an ultraviolet (UV)-transparent pre-polymer coating on the support layer between the optical mirrors and curing the UV-transparent pre-polymer coating; and coupling a UV light source to an injection end of the propagating layer.

Figure 12:
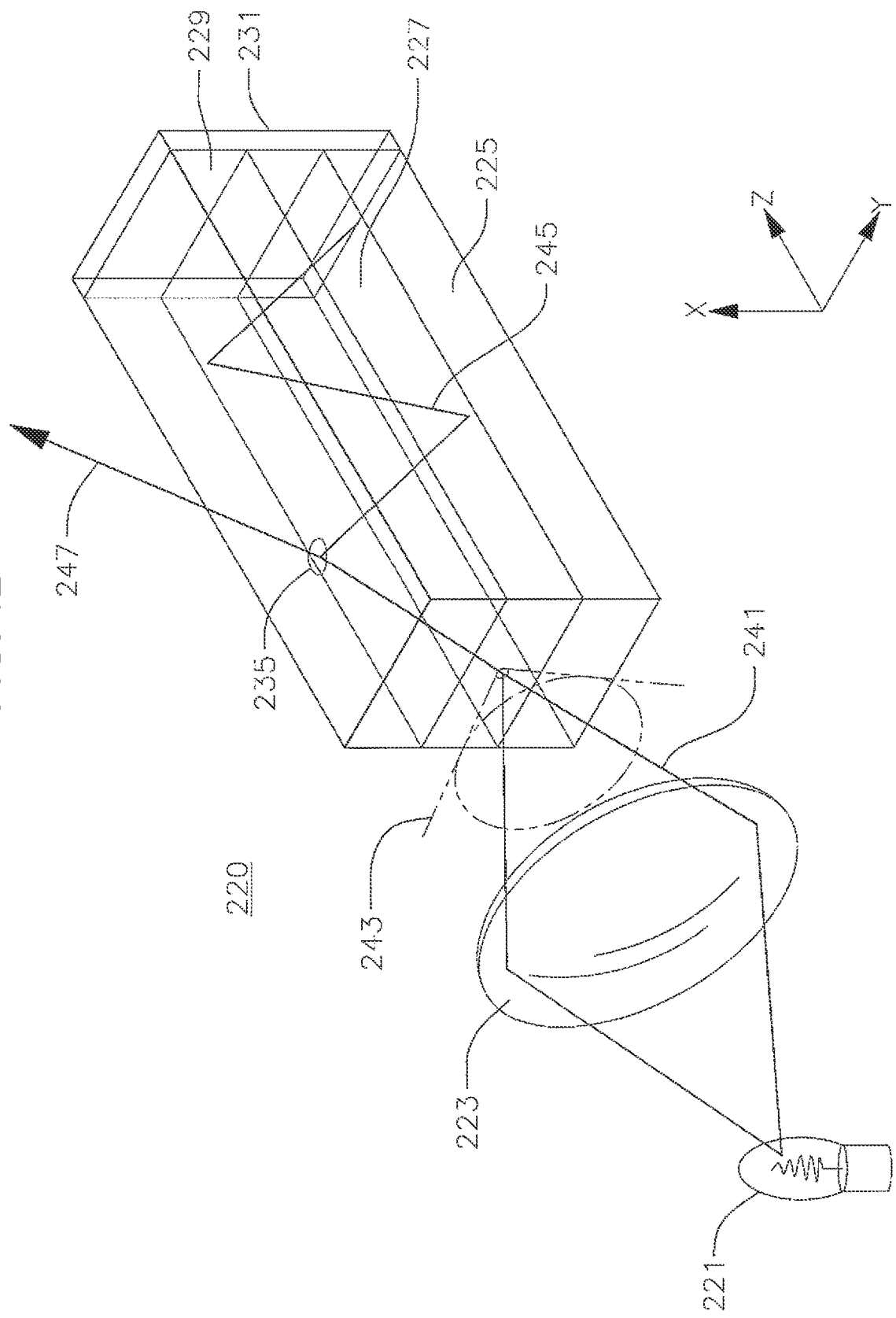
FIG. 12 is a schematic diagram showing a self-sanitizing surface structure including a UV lamp, a focusing lens, and a terminal end mirror as optical components, and a multi-layer structure including a substrate layer, a support layer on the substrate layer, and a propagating layer on the substrate layer.

FIG. 12 is a schematic diagram showing a self-sanitizing surface structure 220 including a UV lamp 221, a focusing lens 223, and a terminal end mirror 231 as optical components, and a multi-layer structure including a substrate layer 225, a support layer 227 on the substrate layer 225, and a propagating layer 229 on the substrate layer 225. UV light 241 is produced by the UV lamp 221, passed through the lens 223, and injected into the propagating layer 229 within the injection angle 243, such that a portion of the light 247 is refracted in the presence of a residue 235, and the remaining portion 245 remains within the propagating layer 229. Each layer of the multi-layer structure may be the same as described herein, according to embodiments of the present disclosure.

Aspects of embodiments of the present disclosure provide a method of decontaminating or reducing contamination on a self-sanitizing surface structure, the self-sanitizing surface structure including a waveguide, and the waveguide including a propagating layer and a support layer that is structured and fabricated according to the methods described herein. The method may include: selecting a wavelength of UV light and a light injection angle; selecting a material for a propagating layer and a material for a support layer; assembling the self-sanitizing surface structure from the selected material for the propagating layer and the selected material for the support layer to form a waveguide; and injecting UV light into the propagating layer at the light injection angle to selectively refract light from a transverse side of the waveguide in the self-sanitizing surface structure.

FIG. 13 is a flowchart or block diagram 250 summarizing the factors and acts included in the method of decontaminating or reducing contamination on a self-sanitizing surface structure utilizing selectively refracted light. Although the acts of selection (251) described herein are listed sequentially, they are not necessarily carried out sequentially or in the recited order; rather, they reflect the simultaneous determination and selection of a combination of parameters, such as those associated with selecting the UV light wavelength and injection angle (253), propagating layer material (255), and support layer material (257), some of which may be constrained by outside factors. Once the parameters have been determined in tandem, the self-sanitizing surface structure is assembled (259), and UV light may be injected into the propagating layer (261).

For example, the wavelength of UV light may be selected (253) by considering the range or specific wavelengths of light produced by a UV light source; the wavelength of light necessary to destroy the residues on the self-sanitizing surface structure; the transparency of the propagating layer to the wavelength of light; the allowable modes of the waveguide, etc., as described above.

The material included in the propagating layer and the thickness of the propagating layer may be suitably selected (255) by considering the transparency of the layer to the wavelength of light necessary to destroy the residues on the self-sanitizing surface structure; the refractive index of the material in relation to the refractive indexes of air, the residue, and the support layer; the desired number of modes in the waveguide (e.g., single mode or multi-mode), ease of deposition, material costs; durability, etc.

The material included in the support layer may be suitably selected (257) by considering the refractive index of the material in relation to the refractive indexes of the propagating layer, residue, and air; ease of deposition, material costs, etc.

The light injection angle may be suitably selected by considering the refractive indexes of the propagating layer, environment, support layer, and residue; the angle of incidence necessary for total reflection to occur, the available modes of the waveguide, etc. As described above, the light should be injected at an angle such that it undergoes TIR under clean conditions, but is refracted in the presence of a residue. The light injection angle may be adjusted using the optics coupling components described herein, include collimating optics, mirrors, refractive lenses, reflective lenses, optical fibers, prisms or gratings, and it will be understood that those having ordinary skill in the art are capable of suitably configuring such components to arrive at the desired light injection angle and to achieve the injecting of UV light into the propagating layer.

The assembling the self-sanitizing surface structure (259) and the injecting UV light into the propagating layer at a suitable light injection angle (261) may be the same as described herein with respect to the self-sanitizing surface structure and the method of fabricating a self-sanitizing surface structure. In some embodiments, the assembling the self-sanitizing surface structure may further include attaching optical components, mirrors, etc., as described herein.

Typical devices including fiber optic cables and other types or kinds of waveguides in the related art have used such waveguides to transmit light from one end of the waveguide to the other (e.g., along the full length of the waveguide). Light is injected into the propagating material via direct contact with a light source at a first end of the waveguide. The waveguide is typically designed or selected (for example, through the use of cladding) so that substantially no light is refracted along the length of the waveguide at all times, e.g. under the range of normal operating conditions. The light thus travels to the opposite end of the waveguide, which may be positioned at or over a desired irradiation target, and is refracted only at that boundary. Changes in the environment along the sides of the waveguide typically do not result in light emission or other optical changes, and/or the waveguides are designed to be unresponsive to such changes. As such, UV light passing through such waveguides in the related art enter and exit the waveguide though longitudinal sides (or ends) of the waveguide, and the exit site of the light typically remains fixed.

In contrast, embodiments of the present disclosure are designed or configured so that selective refraction from one or more points along the sides of the waveguide is possible, and sometimes encouraged, under specific conditions (e.g., in the presence of a residue). Further, embodiments of the present disclosure may be designed or selected so that refraction along the surface structure can be automatically toggled on or off in response to environmental changes, without requiring additional user input such as physical repositioning of the waveguide, recalculating a suitable input, or even flipping a switch. As such, UV light passing through self-sanitizing surface structures according to embodiments of the present disclosure may enter and exit the waveguide though longitudinal sides (or ends) of the waveguide under one set of conditions (e.g., in the absence of a residue), but the exit site of the light may be subsequently located on a transverse side of the waveguide under a second set of conditions (e.g., when a residue is on the transverse side of the waveguide).

Furthermore, embodiments of the present disclosure may be designed or configured as described herein so that refraction does not occur indiscriminately and uniformly across the entire area covered by the self-sanitizing surface structure, but instead occurs only under specific, controlled conditions and with spatial selectivity (e.g., in regions of the waveguide that are in direct contact with a residue via selective refraction, as described in detail herein), thereby reducing the risk of inappropriate light exposure.

In addition, other types or kinds of devices utilizing UV light for sanitation purposes have typically applied the light to surfaces by manually holding or permanently positioning an external UV light source over the surface or item to be sanitized, which can be bulky and inconvenient. Further, such UV light sources are often high power in order to generate sufficient light flux for sanitization. In contrast, embodiments of the present disclosure may provide a permanent self-sanitizing fixture with reduced power requirements compared to conventional methods using an external UV light source.

The following example embodiments are provided solely to aid in understanding of the invention, and are not intended to be limiting in any form.

EXAMPLES

Example 1

A self-sanitizing surface structure configured to selectively emit light is formed by placing a support layer formed of Ag coated Mylar on a structural layer. A propagating layer formed of PCTFE (n=1.435) is thermally bonded to the support. Subsequently, mirrored Al pieces are attached to the longitudinal sides of the support layer and propagating layer. A UV light source including a Hg vapor lamp (UV-C emission at 184 nm and 254 nm) is placed in a mirrored container with an opening mated to a prism that is heat bonded to the PCTFE surface, thereby completing manufacture of a self-sanitizing surface structure.

When the self-sanitizing surface structure of Example 1 is used in air, the critical angle is 44.2°. When the self-sanitizing surface structure is exposed to a residue including water, the critical angle at the point of contamination is 67.9°. Therefore, UV light from the Hg vapor lamp was injected into the propagating layer at an incident angle between 44.2° to 67.9° in order to achieve TIR in clean regions and refraction-aided sanitization in the contaminated region.

Example embodiments of the present disclosure may be suitably used in environments that are frequently exposed to pathogens, are prone to cross-contamination, or may be vulnerable to chemical and biological weapon attack, including lavatories, bathrooms, hospitals, seating areas in publically used or shared vehicles, military bases, ambulances, laboratories, and food preparation facilities.

Example embodiments of the present disclosure may be suitably applied to a wide range of surfaces and surface types, including walls, floors, ceilings, fixtures (such as desks, counters, benches, equipment cabinets, fume hoods, and biological hoods), and portable equipment (such as gurneys and chairs). Further, example embodiments of the present disclosure may be used to disinfect objects pressed against the surface (such as gloves, shoes, clothing, hands, tools, etc.), or may be incorporated into a portable surface that can be pressed against other objects and surfaces, such as those described above.

Figure 14A:
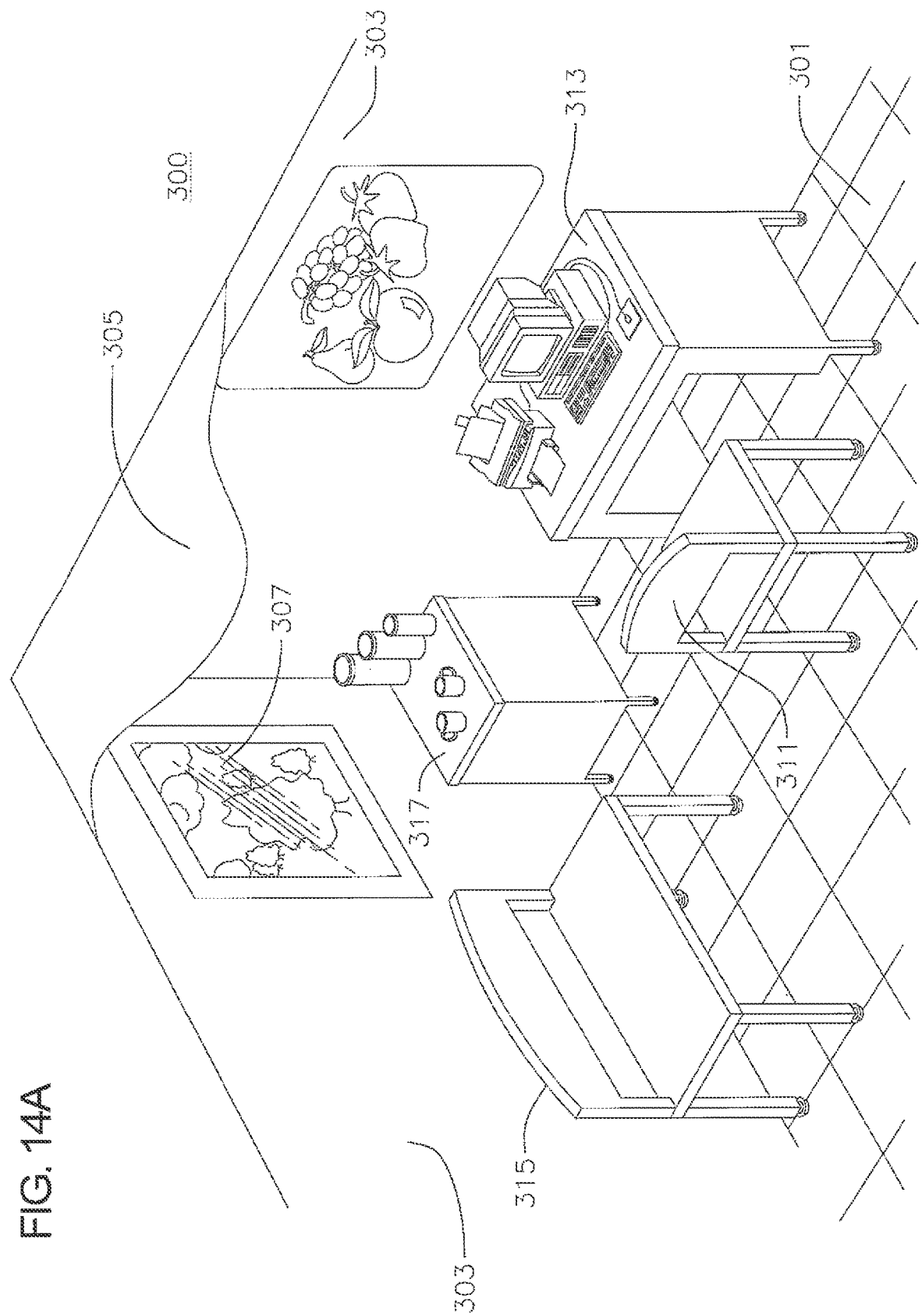
FIGS. 14A-B depict example rooms and surfaces, including an office and a public lavatory, to which self-sanitizing surface structures according to embodiments of the present disclosure may be applied.
Figure 14B:
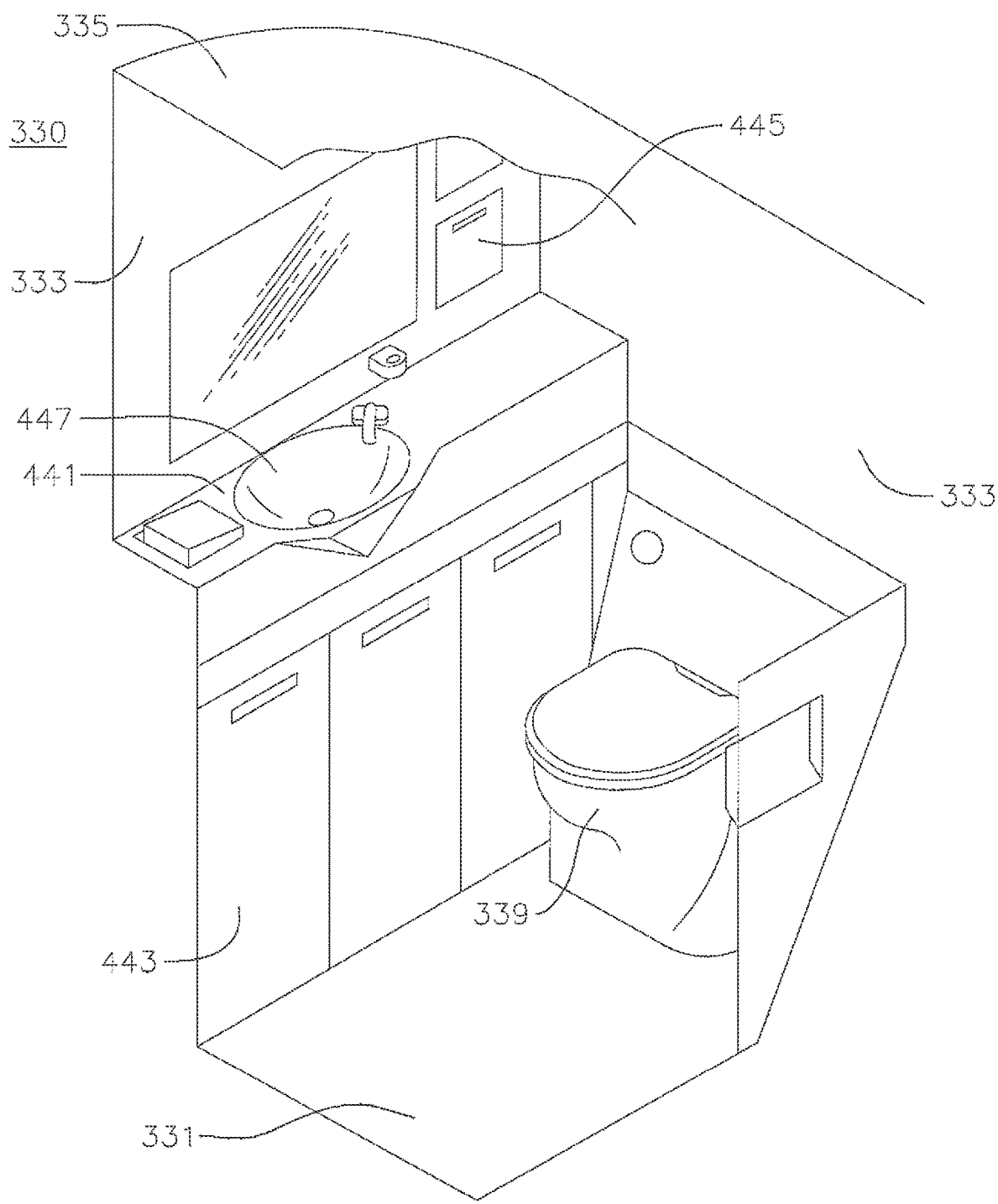

FIGS. 14A-B depict example rooms and surfaces to which self-sanitizing surface structures according to embodiments of the present disclosure may be applied. It will be understood that these images are provided merely for illustration, and do not limit the intended applications or forms of embodiments of the present disclosure. In FIG. 14A, any fixed structural surface of a room or building, including the floors 301, walls 303, ceiling 305, windows 307, etc., may be modified to include self-sanitizing surface structures according to embodiments of the present disclosure. Furthermore, the surfaces of movable furniture items, including chairs 311, desks 313, benches 315, and countertops 317 may also modified to include self-sanitizing surface structures according to embodiments of the present disclosure. In FIG. 14B, depicting a public lavatory 330, any structural surface including the floors 331, walls 333, ceiling 335, etc., may be modified to include self-sanitizing surface structures according to embodiments of the present disclosure. Furthermore, any utility surfaces including the toilet 339, countertop 441, cabinet doors 443, trash receptacle door 445 (including its handle), and wash basin 447, may also modified to include self-sanitizing surface structures according to embodiments of the present disclosure. As can be observed from the toilet 339 and wash basin 447, the surfaces modified to include a self-sanitizing surface structures may be planar or may be curved. Indeed, self-sanitizing surface structures according to embodiments of the present disclosure may be widely applied to various human-built environments and objects as a versatile and safe means of surface sanitization.

As used herein, unless otherwise expressly specified, all numbers such as those expressing values, ranges, amounts or percentages may be read as if prefaced by the word "about", even if the term does not expressly appear. As used herein, the terms "substantially", "about", "nearly", and similar terms are used as terms of approximation and not as terms of degree, and are intended to account for the inherent deviations in measured or calculated values that would be recognized by those of ordinary skill in the art. Plural encompasses singular and vice versa. For example, while the present disclosure may describe "an" oligomer or "a" photopolymer, a mixture of such oligomers or photopolymers can be used. Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. As used herein, the terms "combination thereof" and "combinations thereof" may refer to a chemical combination (e.g., an alloy or chemical compound), a mixture, or a laminated structure of components.

It will be understood that although the terms "first", "second", "third", etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

Spatially relative terms, such as "beneath", "below", "lower", "under", "above", "upper", and the like, may be used herein for ease of explanation to describe one element or feature's relationship to another element(s) or feature(s) as illustrated in the accompanying drawings. It will be understood that the spatially relative terms are intended to encompass different orientations of the device in use or in operation, in addition to the orientations depicted in the accompanying drawings. For example, if the structures in the accompanying drawings are turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including", when used in this specification, specify the presence of the stated features, integers, acts, operations, elements, and/or components, but do not preclude the presence or addition of one or more other features, integers, acts, operations, elements, components, and/or groups thereof. As used herein, the term "and/or" includes any and all combinations of one or more of the associated listed items. Expressions such as "at least one of", when preceding a list of elements, modify the entire list of elements and do not modify the individual elements of the list. Further, the use of "may" when describing embodiments of the inventive concept refers to "one or more embodiments of the inventive concept." As used herein, the terms "use," "using," and "used" may be considered synonymous with the terms "utilize," "utilizing," and "utilized," respectively.

While the subject matter of the present disclosure has been described in connection with certain embodiments, it is to be understood that the subject matter of the present disclosure is not limited to the disclosed embodiments, but, on the contrary, the present disclosure is intended to cover various modifications and equivalent arrangements included within the spirit and scope of the appended claims, and equivalents thereof.

What is claimed is:

1. A method of fabricating a self-sanitizing surface structure, the self-sanitizing surface structure comprising a waveguide; the waveguide comprising: a propagating layer having a first transverse side and a second transverse side opposite the first transverse side, the first transverse side being exposed to air and configured to selectively refract light; and a support layer in direct contact with the second transverse side of the propagating layer, the waveguide being configured to selectively refract about 0.01% to about 25% of the flux of an ultraviolet (UV) light injected into the propagating layer, the selective refraction occurring when a residue is on the first transverse side and at an interface between the first transverse side and the residue, the method comprising:

attaching optical mirrors to a substrate, the optical mirrors having a height larger than that of the substrate;

forming the propagating layer by applying an ultraviolet (UV)-transparent pre-polymer coating between the optical mirrors and curing the UV-transparent pre-polymer coating;

attaching the support layer to the substrate;

attaching the propagating layer to the support layer; and coupling a UV light source to an injection end of the propagating layer.

2. The method of claim 1, wherein the UV-transparent pre-polymer coating comprises monomers and oligomers.

3. The method of claim 1, wherein the applying the UV-transparent pre-polymer coating comprises a task selected from the group consisting of spraying, spin-coating, dip coating, and evaporation.

4. The method of claim 1, wherein the curing the UV-transparent pre-polymer coating comprises heating and/or UV-irradiation.

5. The method of claim 1, further comprising depositing a metal layer on the propagating layer, the metal layer being configured to generate surface plasmon polaritons (SPPs).

6. The method of claim 1, wherein the support layer comprises a metal layer, a diffuse reflector layer, a transparent solid material, or a layer of gas.

* * * * *